US007589455B2

(12) United States Patent
Adachi et al.

(10) Patent No.: US 7,589,455 B2
(45) Date of Patent: Sep. 15, 2009

(54) CAPACITIVE MICROMACHINED ULTRASONIC TRANSDUCER AND PRODUCTION METHOD OF SAME

(75) Inventors: Hideo Adachi, Tokyo (JP); Katsuhiro Wakabayashi, Tokyo (JP); Kazuya Matsumoto, Tokyo (JP); Ryo Ota, Tokyo (JP); Masaaki Amikura, Tokyo (JP); Hiroshi Ito, Tokyo (JP); Mamoru Hasegawa, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 47 days.

(21) Appl. No.: 11/942,364

(22) Filed: Nov. 19, 2007

(65) Prior Publication Data

US 2008/0067895 A1 Mar. 20, 2008

Related U.S. Application Data

(63) Continuation of application No. PCT/JP2006/310270, filed on May 23, 2006.

(30) Foreign Application Priority Data

May 31, 2005 (JP) ............................. 2005-159582

(51) Int. Cl.
 *H01L 41/09* (2006.01)
(52) U.S. Cl. ..................................................... 310/335
(58) Field of Classification Search ................. 310/335, 310/320, 324, 327, 311, 309, 366, 365; 367/155, 367/181; *H01L 41/09*
See application file for complete search history.

(56) References Cited

U.S. PATENT DOCUMENTS 6,246,158 B1* 6/2001 Ladabaum ................. 310/334

| 6,909,221 B2* | 6/2005 | Ayazi et al. .................. 310/324 |
| 7,449,821 B2* | 11/2008 | Dausch ........................ 310/365 |
| 2004/0100163 A1* | 5/2004 | Baumgartner et al. ....... 310/334 |
| 2004/0174773 A1 | 9/2004 | Thomenius et al. |

FOREIGN PATENT DOCUMENTS

| JP | 2000-028595 | 1/2000 |
| JP | 2002-159492 | 6/2002 |
| JP | 2003-325507 | 11/2003 |
| JP | 2003-325526 | * 11/2003 |
| JP | 2004-274756 | 9/2004 |
| JP | 2004-350700 | * 12/2004 |
| JP | 2004-350701 | 12/2004 |
| JP | 2006-122188 | 5/2006 |
| JP | 2006-198240 | 8/2006 |

* cited by examiner

*Primary Examiner*—Thomas M. Dougherty
*Assistant Examiner*—Karen B Addison
(74) *Attorney, Agent, or Firm*—Scully, Scott, Murphy & Presser, P.C.

(57) ABSTRACT

A capacitive micromachined ultrasonic transducer (cMUT) is constituted by a plurality of transducer elements comprising plural transducer cells that are mutually connected in parallel and comprises: a silicon substrate; a bottom electrode placed on the top surface of the silicon substrate; an upper electrode placed opposite to the bottom electrode and apart therefrom by a prescribed air or vacuum; a membrane for supporting the bottom electrode; and a membrane supporting part for supporting the membrane, wherein the cMUT comprises a third electrode which has an electrical continuity to the bottom electrode and which corresponds to either one of the transducer cells of a prescribed number of the transducer subelement or of the transducer elements, and a fourth electrode which is a ground electrode electrically connected to the bottom electrode.

27 Claims, 20 Drawing Sheets

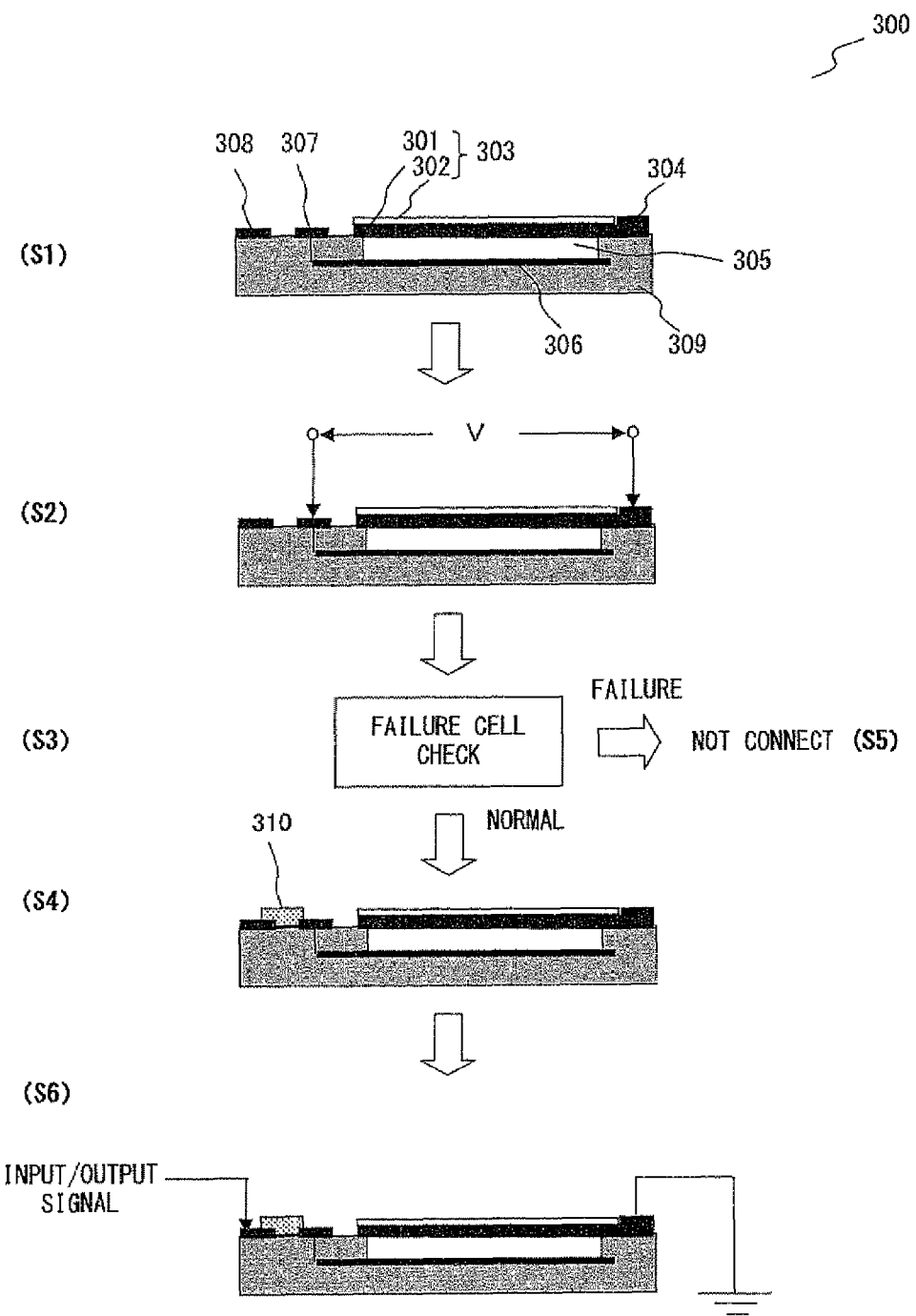
F I G. 1

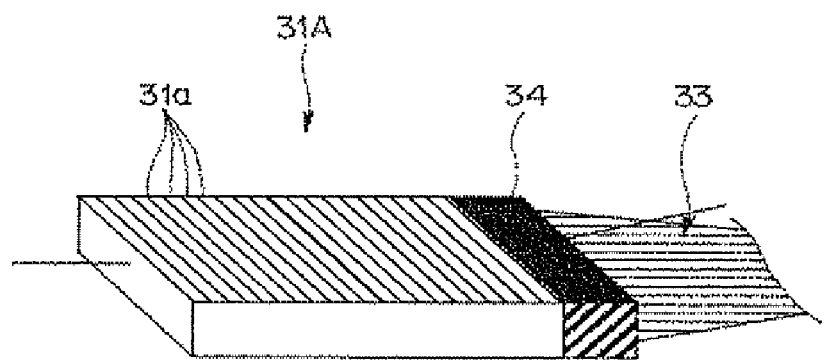
F I G. 4

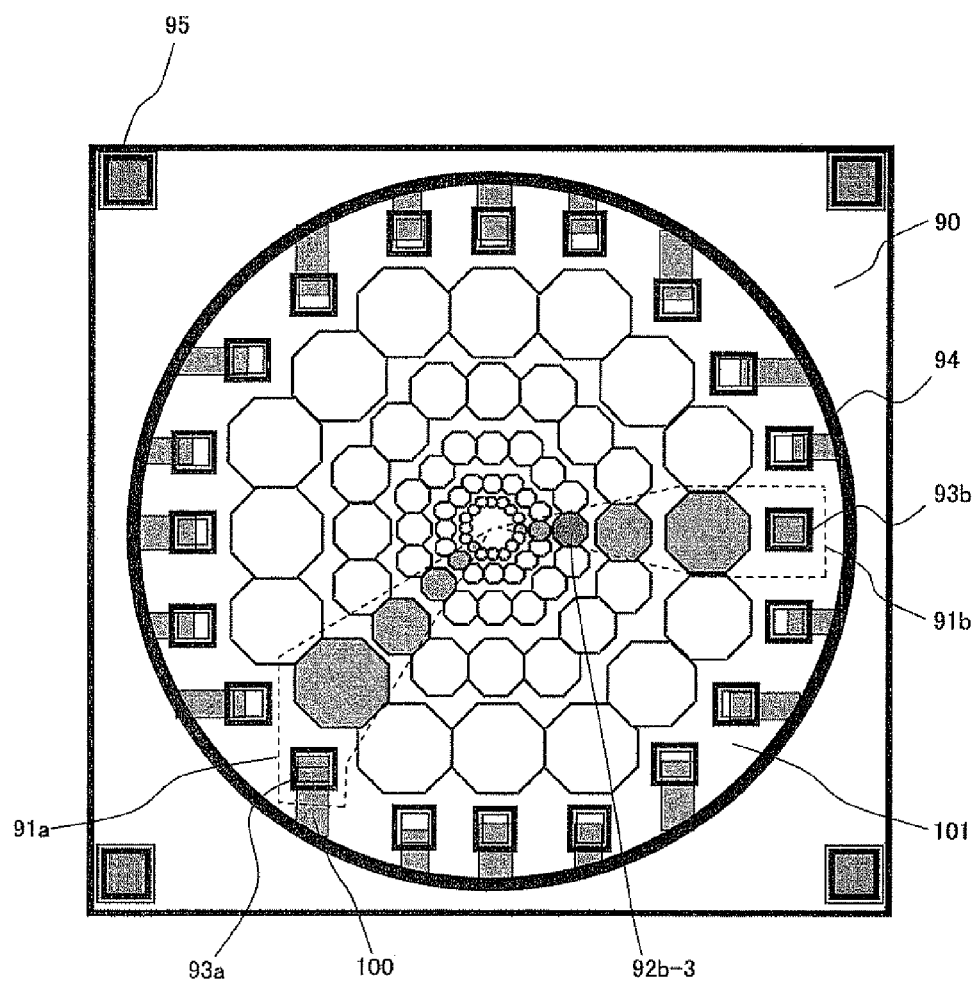
F I G. 1 0

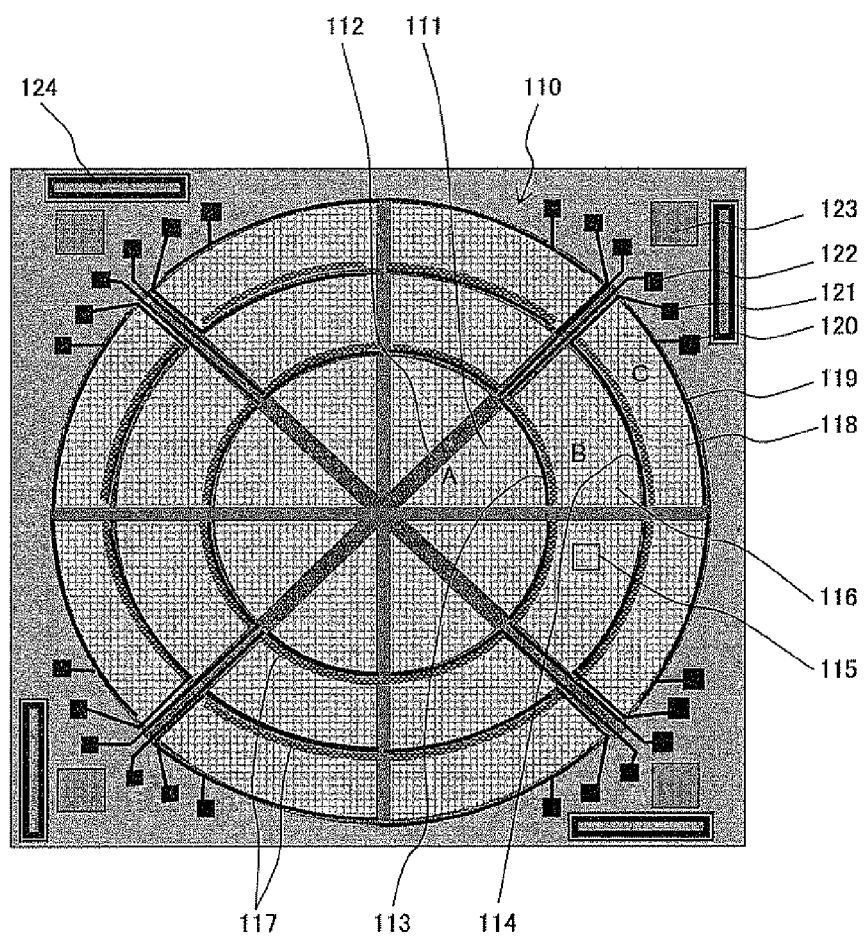
F I G. 1 1

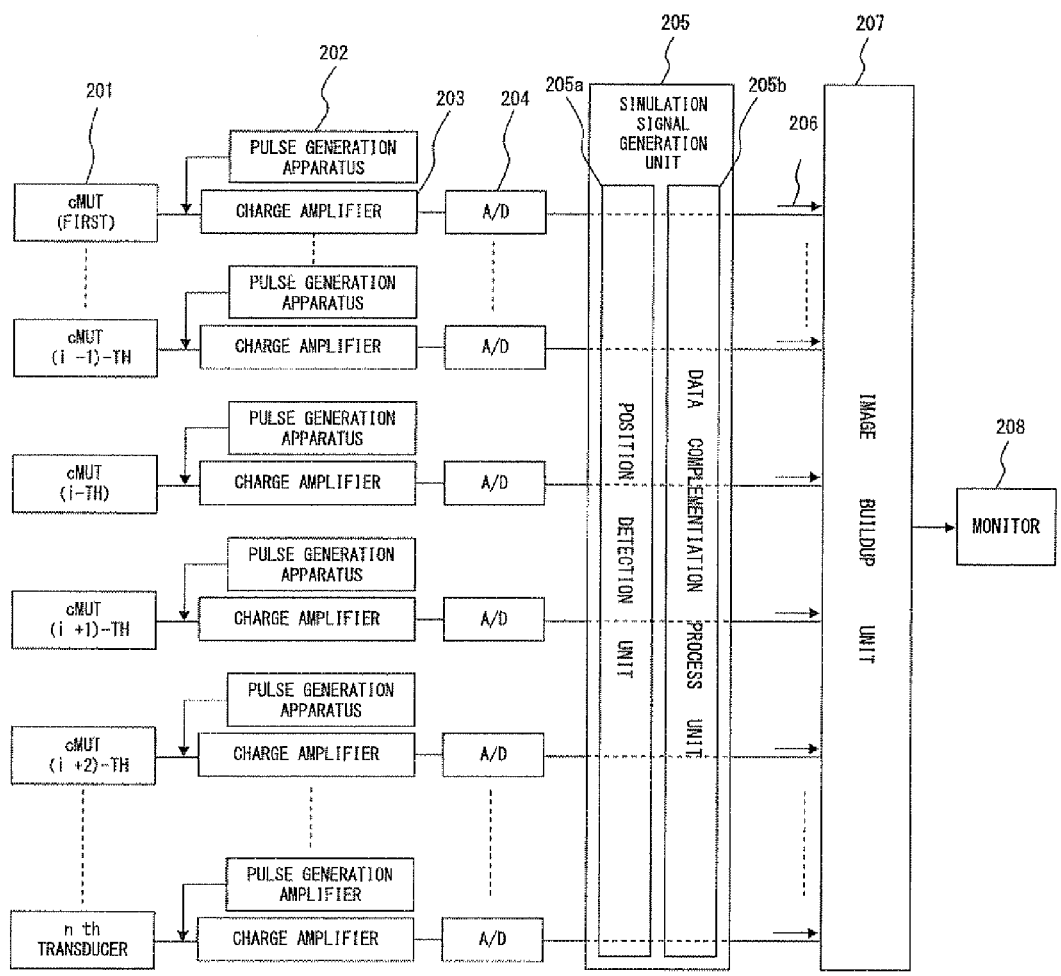
F I G. 18

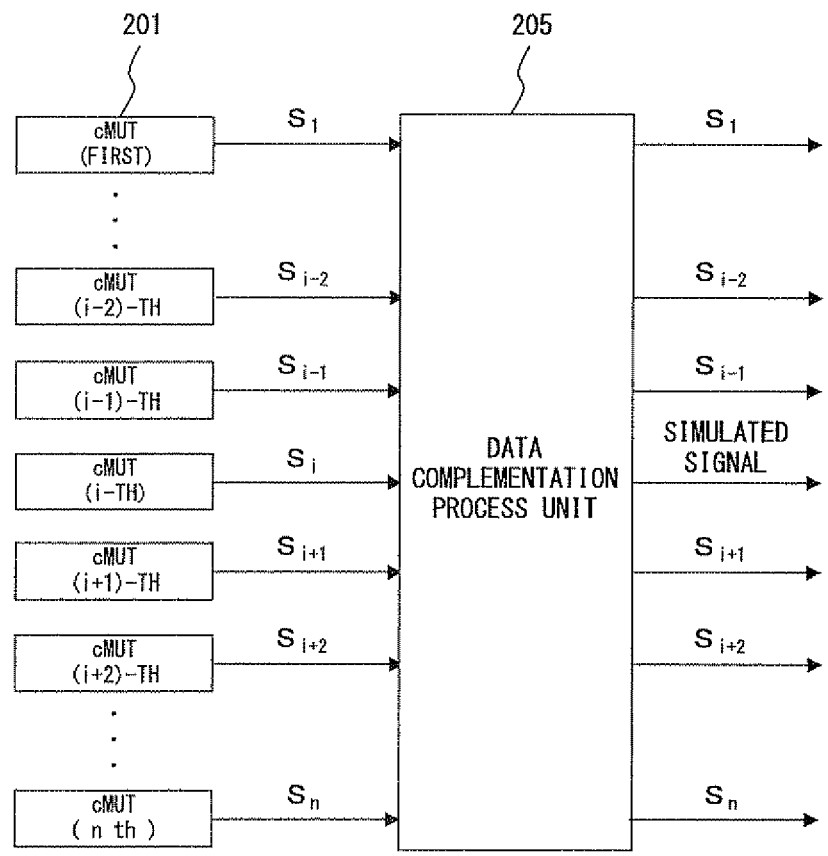
F I G. 19

CAPACITIVE MICROMACHINED ULTRASONIC TRANSDUCER AND PRODUCTION METHOD OF SAME

CROSS REFERENCE TO RELATED APPLICATION

This is a Continuation Application of PCT Application No. PCT/JP006/310270, filed on May 23, 2006, which was not published under PCT Article 21(2) in English.

This application is based on and claims the benefit of priority from the prior Japanese Patent Application No. 2005-159582 filed in Japan on May 31, 2005, the entire contents of which are incorporated by this reference.

BACKGROUND OF THE INVENTION

1. Field of the Invention

The present invention relates to a capacitive micromachined ultrasonic transducer (cMUT).

2. Description of the Related Art

An ultrasonic diagnosis method in which an ultrasound is transmitted toward an internal wall of a body cavity and a state of the interior of a human body is diagnosed by imaging it with an echo signal of the ultrasound is popular. One type of equipment used for the ultrasonic diagnosis method is an ultrasonic endoscope (e.g., refer to reference Laid-Open Japanese Patent Application Publication No. 2004-350701).

The ultrasonic endoscope is equipped with an ultrasonic probe at the head of an insertion tube which is to be inserted into a body cavity. The ultrasonic probe is for converting an electric signal into an ultrasound, transmitting it to a body cavity and converting an ultrasound into an electric signal by receiving the ultrasound reflected from the body tissue.

While a conventional ultrasonic probe uses the ceramic lead zirconate titanate (PZT) as a piezoelectric element for converting an electric signal into an ultrasound, recently receiving attention is a Capacitive Micromachined Ultrasonic Transducer (simply noted as "cMUT" hereinafter) which is produced using a silicon micromaching process. This is one of devices generically called a Micro Electro-Mechanical System (MEMS).

The cMUT is collectively featured with a plurality of cMUT cells with the electric terminal of each cMUT cell being parallelly connected so as to constitute a unit of the cMUT element which is a unit for signal controlling. Furthermore, a large number of the cMUT elements are arrayed, thus constituting a cMUT.

SUMMARY OF THE INVENTION

A cMUT according to the present invention is one which is constituted of a plurality of transducer elements comprising plural transducer cells that are mutually connected in parallel and which comprises: a silicon substrate; a bottom electrode placed on the top surface of the silicon substrate; an upper electrode placed opposite to the bottom electrode and separated therefrom by a prescribed air or vacuum; a membrane for supporting the upper electrode; and a membrane supporting part for supporting the membrane, wherein the cMUT comprises a first electrode pad which is the one corresponding to either one of each of the transducer cells, each of a plurality of transducer subelement constituted by a group of the transducer cells or each of the transducer elements and which has an electrical continuity to the bottom electrode, and a second electrode pad which is a ground electrode electrically connected to the upper electrode.

According to the present invention, a production method of a cMUT which is constituted of a plurality of transducer elements comprising plural transducer cells that are mutually connected in parallel and which comprises a silicon substrate, an bottom electrode placed on the top surface of the silicon substrate, an upper electrode placed opposite to the bottom electrode and separated therefrom by a prescribed air or vacuum, a membrane for supporting the upper electrode and a membrane supporting part for supporting the membrane. This production method equips a first electrode pad, which is the one corresponding to either one of the transducer cells, to each of a plurality of transducer subelement constituted by a group of the transducer cells or to each of the transducer elements and which has an electrical continuity to the bottom electrode; and a second electrode pad which is a ground electrode electrically connected to the upper electrode.

According to the present invention, a body cavity insertion type ultrasonic diagnosis apparatus having an ultrasonic transducer element incorporating a cMUT arraying a plurality of ultrasonic transducer elements comprises: a position detector for detecting position information of the ultrasonic transducer element on the basis of an ultrasonic echo signal obtained from the ultrasonic transducer element; a analog/digital (A/D) converter for simulatively generating an ultrasonic echo signal for complementing a missing ultrasonic echo signal if a missing one exists; and an imaging unit for building up an ultrasonic diagnosis image on the basis of a simulated ultrasonic echo signal generated by the analog/digital (A/D) converter.

According to the present invention, a body cavity insertion type ultrasonic diagnosis apparatus having an ultrasonic transducer element incorporating a cMUT arraying a plurality of ultrasonic transducer elements comprises: an imaging unit for building up an ultrasonic diagnosis image on the basis of an ultrasonic echo signal obtained from the cMUT; an abnormal zone detection unit for detecting a zone with an abnormal brightness by means of image processing on the basis of the ultrasonic diagnosis image; and a brightness correction unit for correcting the brightness of the detected zone with an abnormal brightness by means of image processing.

According to the present invention, a cMUT exists which is constituted of a plurality of transducer elements comprising plural transducer cells that are mutually connected in parallel and which comprises a silicon substrate, a bottom electrode placed on the top surface of the silicon substrate, an upper electrode placed opposite to the electrode and separated therefrom by a prescribed air or vacuum, a membrane for supporting the upper electrode and a membrane supporting part for supporting the membrane. The cMUT is configured by a two-terminal construction which is constituted of a first electrode pad, which is the one corresponding to each of the transducer subelement, a plurality of which exist comprising a group of the transducer cells and have an electrical continuity to the bottom electrode; a second electrode pad which is a ground electrode electrically connected to the upper electrode; a first terminal electrically connected to all of the first electrode pads; and a second terminal electrically connected to all of the second electrode pads.

BRIEF DESCRIPTION OF THE DRAWINGS

FIG. 1 is a conceptual diagram about a method of seeking a defect cell in a cMUT element according to the first embodiment;

FIG. 4 shows an external view of a cMUT array type ultrasonic transducer according to the first embodiment;

FIG. 10 exemplifies a cMUT element after wire-connecting a signal electrode pad interconnected from cell group to a common signal wiring according to the second embodiment;

FIG. 11 exemplifies another cMUT element before wire-connecting a signal electrode pad interconnected from cell group to a common signal wiring according to the second embodiment;

FIG. 18 illustrates a diagram of an intra-body cavity ultrasonic diagnosis apparatus comprising an pseudo signal process circuit for interpolating a missing ultrasonic echo signal among ultrasonic echo signals output from a transducer element according to the fourth embodiment;

FIG. 19 is a diagram describing a function of a data interpolation process unit according to the fourth embodiment.

DESCRIPTION OF THE PREFERRED EMBODIMENTS

Figure 2:
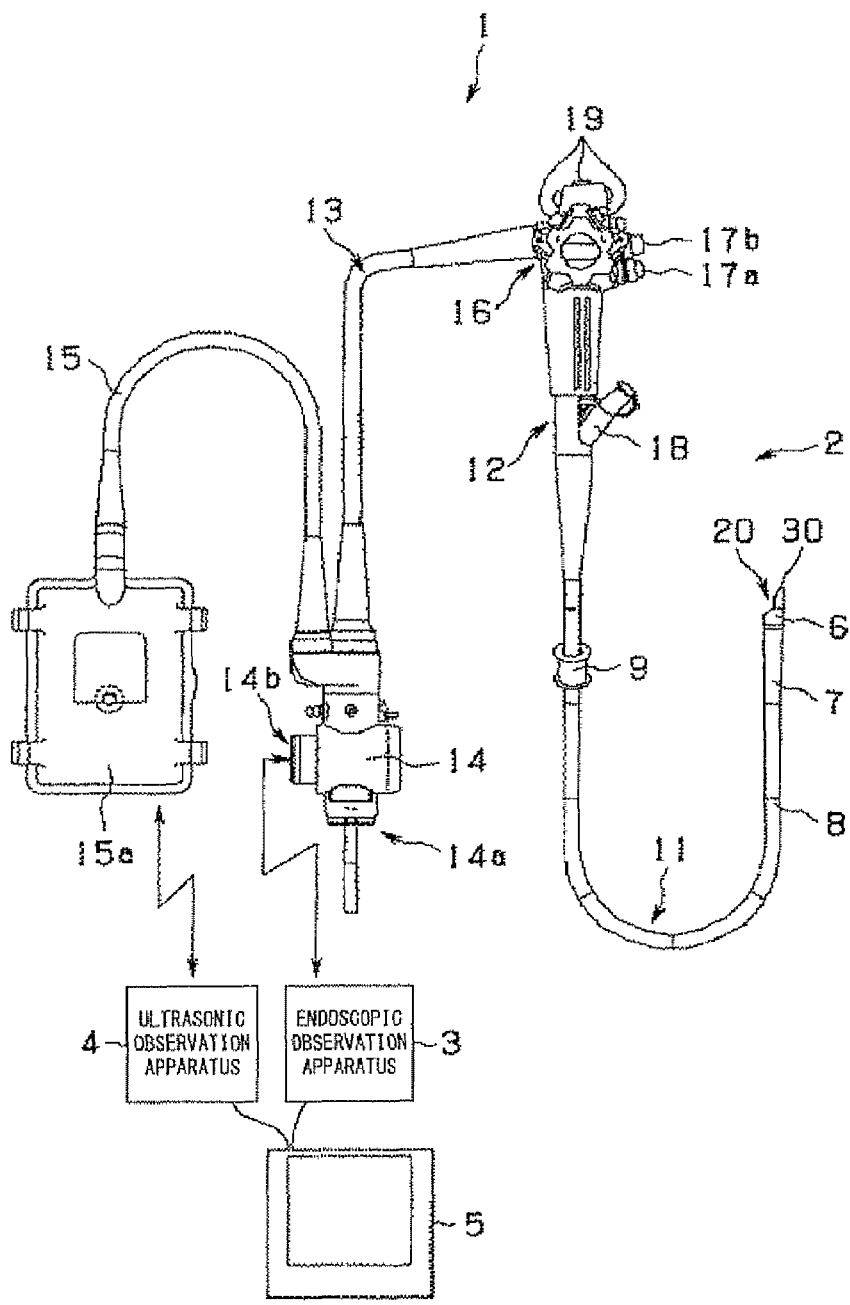
FIG. 2 shows a system configuration of an intra-body cavity ultrasonic diagnosis apparatus according to the first embodiment.

Since a large number of cMUT cells, cell group or elements are parallelly connected together, a shorting in even one of them causes a shorted state in the entirety of the elements or ultrasonic transducer, resulting in a state of inoperability.

Meanwhile, the cMUT, being featured with a large number of cells with a small surface size, requires that a failure in a small number of cMUT cells, subelement or elements not sacrifice a large number of functioning cMUT cells, subelement or elements, so as to cause them to operate normally.

As an example, the present embodiment of the present invention is described as a cMUT detecting a defect cell, defect cell group or defect element or subelement, and inputting and outputting a signal to and from a normal cell, cell group or element on the basis of the detection results.

First Embodiment

The present embodiment is described as a method for checking whether or not there is a failure in each of the cMUT elements or subelement, detecting for a defect cMUT element or a defect subelement and wire-connecting only the defect free cMUT element or subelement to an electrode pad of a common signal wiring, before wire-connecting the electrode pad of each cMUT element or subelement, in a process similar to the final process of a cMUT production.

FIG. 1 is a conceptual diagram of checking a defect cell of a cMUT according to the present embodiment. First, the process before completing a cMUT element forms a cell and equips each cell (or cell group) with a signal input/output electrode pad (S1).

The description here is of the process of S1. A cMUT element 300 is generally constituted of a silicon substrate 309 having a cavity (i.e., an air or vacuum gap part) 305 and by a membrane 303 positioned above the cavity 305. The bottom of the cavity 305 is equipped with a bottom electrode 306. The membrane 303 is generally constituted of an upper electrode 301 opposite to the bottom electrode 306 and a protective film 302 for covering the upper electrode 301.

The cavity 305 is defined as a space enclosed between the membrane 303 and concave part of the silicon substrate 309. Also, the membrane 303 including the upper electrode 301 and the silicon substrate including the bottom electrode for each cavity refer to a cell. FIG. 1 shows only one cell; in the actual configuration, however, a silicon substrate is featured with a very large number of cells.

A drive signal is transmitted to a plurality of subelement so as to drive them simultaneously, and the unit for driving and controlling is called a transducer element.

While the primary configuration of a cMUT is described above, it is further equipped with a signal electrode pad 307 electrically connected to the bottom electrode 306 for exposing it to a silicon substrate 309 on the membrane side. Moreover, the signal electrode pad 307 is equipped with a common signal interconnect 308 separate therefrom. Also a common ground electrode pad 304 electrically connected to the upper electrode 301 is equipped for exposing it on the surface of the membrane 303.

Next is to check for a defect cell (noted as "defect cell check" hereinafter) for each cell (or cell group) (S2 and S3). The defect cell check is to detect whether or not there is a failure such as a shorting in cells before wire-connecting the signal electrode pad 307 to the common signal interconnect 308. The reason is that, if there is a shorting in either of the cells, the entirety of the cMUT element or even that of the ultrasonic transducer is possibly shorted because the plurality of cells are mutually connected in parallel. Accordingly, whether or not there is a failure such as a shorting in cells is detected by using various methods. Note that a defect cell due to shorting is referred to as a defect cell.

An outline of the defect cell check is as follows. First, a voltage is applied between the signal electrode pad 307 and common signal interconnect 308 in order to apply a voltage between the upper electrode 301 and bottom electrode 306 (S2).

If there is a spot where shorting occurs between the upper electrode 301 and bottom electrode 306 in this event, the capacitance and dielectric loss, or DC resistance, is different only for this spot; in other words, applying a voltage does not cause a charge to accumulate (i.e., it fails to charge up).

Therefore, an application of a voltage between the signal electrode pad 307 and common signal interconnect 308 and a measurement of the capacitance and dielectric loss, that of the DC resistance, or that of the accumulation of charge, between the upper electrode 301 and bottom electrode 306 make it possible to detect a defect cell (S3).

An example of the defect cell check is a method for detecting whether or not there is a failure such as a shorting occurring in a cell by measuring a capacitance and a dielectric loss by using an inductance-capacitance-resistance (LCR) meter or such. This method contacts the measurement probe of an LCR meter between the signal electrode pad 307 and common signal interconnect 308 for applying an AC voltage between them in order to apply a voltage between the upper electrode 301 and bottom electrode 306, thereby measuring the capacitance and dielectric loss.

Note that the capacitance and dielectric loss may alternatively be measured by using an LCR meter or such by applying a DC voltage (i.e., a DC bias) in addition to the AC voltage as described above. This is for responding to a harmonic imaging diagnosis. For a harmonic imaging, a wider band is required of an ultrasonic transducer. For that purpose, a high DC bias voltage needs to be overlapped in addition to applying a high voltage pulse to the cMUT. The reason is that a transducer cell might not breakdown until an application of a DC bias voltage.

Another example of the defect cell check is a method for detecting whether or not there is a failure, such as a shorting occurring in a cell, by measuring DC resistance using an LCR meter or such. This method applies a DC voltage between the signal electrode pad 307 and common signal interconnect 308 by contacting the measurement probe of the LCR meter between them in order to apply a voltage between the upper electrode 301 and bottom electrode 306, thereby measuring the DC resistance.

Yet another example of the defect cell check is a method for detecting whether or not there is a failure such as a shorting occurring in a cell by means of a noncontact infrared temperature inspection. First, a voltage is applied between the common signal interconnect 308 and the common ground electrode pad 304. If there is a spot of shorting between the upper electrode 301 and bottom electrode 306 in this event, an application of a voltage causes a temperature increase or radiance in the shorted spot, which is a known phenomenon, thereby making it possible to inspect for a failure such as a shorting.

Therefore, the application of a voltage between the common signal interconnect 308 and the common ground electrode pad 304 and an image observation of a heat-up or radiance spot on the element by using an infrared image sensor coupled with a microscope (e.g., a thermo viewer) make it possible to detect a defect cell.

Yet another example of the defect cell check is a method for detecting whether or not there is a failure such as a shorting occurring in a cell by means of image inspection using an electron beam. This method makes it possible to detect a defect cell by observing how a charge is accumulated because the charge is accumulated (i.e., charging up) via an application of voltage if there is no spot of shorting between the upper electrode 301 and bottom electrode 306.

This method scans the surface of a transducer by narrowing down an electron beam as used in a semiconductor process. As a result of the scan, the detected voltage, resistance and such are imaged as a map of accumulated charge so that a position of a defect cell and a degree of the failure are judged on the basis of a pattern, or such, of the obtained image, e.g., a brightness pattern.

As an example of the process of S2 and S3, the cMUT 300 is observed by using a scanning electron microscope (SEM) in a vacuum for example. An emission of an electron beam on a specimen by using an SEM generates a secondary electron from the surface of the specimen. A scan of a narrowed down incident electron beam on the surface of the specimen and a conversion of the generated secondary electron volume into a brightness signal make it possible to obtain a targeted SEM image.

The use of the SEM makes it possible to obtain a high brightness SEM image as a result of a normal cell (i.e., not shorted) being charged up. A defect cell on the other hand is not charged up, causing an SEM image to be a low brightness.

As another example of the process of S2 and S3, the use of an Electron Beam Induced Current (EBIC) enables a detection of a difference of an electrical potential state as, for example, image information.

The EBIC method is mainly used for a junction failure analysis of an interior of a semiconductor. The energy of an electron beam forms an electron/hall pair, and the formed electron and hall flow inversely due to an internal field of the depletion layer. A current caused by the internal field is called an electron beam induced current. The electron beam induced current is sensitive to a crystal structure defect so that a detection of the EBIC signal makes it possible to evaluate a cell breakdown caused by a crystal structure defect.

Applying a potential between the signal electrode pad 307 and common signal interconnect 308 of a silicon substrate and obtaining an image by means of the EBIC method make conductors of different potentials display different contrasts, thereby making it possible to discern between a shorted cell part (i.e., a defect cell) and other cells (i.e., normal cells).

Incidentally, an imaging method using an electron beam may employ a voltage contrast method, a Specimen Absorbed Current method, an Electron beam induced current method, or a resistance contrast imaging (RCI) method, which are known methods employed for a semiconductor process, in lieu of being limited to using an SEM or EBIC method.

If a normal cell is detected as a result of the defect cell check, an interconnect combining cells and common signal 310 is formed for electrically connecting between the signal electrode pad 307 and the common signal interconnect 308 (S4).

If a defect cell is detected as a result of the defect cell check, the process of the S4 is not carried out for the cell (S5). That is, the signal electrode pad 307 and the common signal interconnect 308 are not wire-connected.

This completes a check for a defect cell for one cell. Carrying out the processes of S2 through S5 results in only the signal electrode pad 307 of a normal cell(s) (or normal cell group) being electrically connected to the common signal interconnect 308.

As the final step in the process, the surface of the cMUT is covered with a protective film or such (S6). Then, a signal is input, or output, from the common signal interconnect 308 by grounding the upper electrode 301. Then a voltage is applied to a pair of electrodes of the upper electrode 301 and bottom electrode 306, attracting the electrodes to each other, and thereafter reducing the voltage to zero causes them to cease to be attracted to each other.

As such, the membrane 303 oscillates to generate an ultrasound and transmits it toward the upper direction of the membrane 303.

The present invention is contrived to suppress damage to other normal transducer cells while simply making the detected defect cell inoperable, thereby making it possible to prevent a shorting and subsequent inoperability for the entirety of elements or the entirety of an ultrasonic transducer.

Next is a description of the details of the present embodiment.

FIG. 2 shows a system configuration of an intra-body tissue ultrasonic diagnosis apparatus according to the present embodiment. An ultrasonic endoscope apparatus 1 comprises an ultrasonic endoscope 2, an endoscopic diagnostic equipment 3, an ultrasonic diagnostic equipment 4 and a monitor 5.

The ultrasonic endoscope 2 comprises a later described cMUT. The endoscopic diagnostic equipment 3 comprises a light source unit and a signal process unit. The light source unit supplies an illuminating light. The signal process unit of the endoscopic diagnostic equipment 3 drives an image pickup element positioned at the distal section of the ultrasonic endoscope, applies various signal processes to an electric signal transmitted from the image pickup element, and generates a video image signal for an endoscopic observation image.

The ultrasonic diagnostic equipment 4 comprises a signal process unit. The signal process unit of the ultrasonic diagnostic equipment 4 drives the cMUT, applies various signal processes to an electric signal transmitted from the cMUT, and generates a video image signal for an ultrasonic tomographic image. The monitor 5 displays an observation-use image on the basis of a video image generated by the ultrasonic diagnostic equipment 4 and endoscopic diagnostic equipment 3.

The ultrasonic endoscope 2 comprises an insertion tube 11, a control section 12 and a universal cord 13. The insertion tube 11 is a slender part to be inserted into a body tissue. The control section 12 is positioned on the base end of the insertion tube 11. The universal cord 13 is extended from the side part on the control section 12. The base part of the universal cord 13 is equipped with an endoscope connector 14 which is to be connected to the endoscopic diagnostic equipment 3. The distal section of the endoscope connector 14 is equipped with an illumination-use connector 14a which is to be connected to the light source part of the endoscopic diagnostic equipment 3. The side part of the endoscope connector 14 is equipped with an electric connector 14b to be detachably attached to an electric cord (not shown in a drawing herein) that is to be electrically connected to the signal process unit.

An ultrasonic cable 15 is extended from the base part of the endoscope connector 14. The ultrasonic cable 15 comprises an ultrasonic connector 15a to be electrically connected to the ultrasonic diagnostic equipment 4.

The insertion tube 11 is constituted of a distal section 6, a bending module 7, and a flexible tube 8 in sequence from the tip side. The distal section 6 is formed with a hard member. The bending module 7 is a freely curved part serially connected to the base part of the distal section 6. The flexible tube 8 is a slim and long part having flexibility and extending to the distal section of the control section 12 by serially connecting itself to the base part of the bending module 7.

The distal section 6 is equipped with an endoscopic observation part 20 and an ultrasonic imaging unit 30. The endoscopic observation part 20 is furnished with an observation optics part and an illumination optics part for performing an endoscopic observation under a direct vision. The ultrasonic imaging unit 30 is featured with an ultrasound scan surface by arraying a plurality of ultrasonic transducers transmitting and receiving an ultrasound.

The control section 12 is equipped with an angulation control knob 16 an air/water valve 17a, a suction valve 17b, a instrument channel port 18, various operation switches 19, et cetera. The angulation control knob 16 is for performing a curvature control of the bending module 7. The air/water valve 17a is for providing an air supply and a water supply.

The suction valve 17b is for performing a suction operation. The instrument channel port 18 is an entrance of a treatment instrument for introducing it into a body tissue. The various operation switches 19 are switches for converting display images to be displayed in the monitor 5 and instructing a freeze, release or such. Incidentally, the numeral sign 9 shows a mouth piece placed in a patient's mouth.

Figure 3:
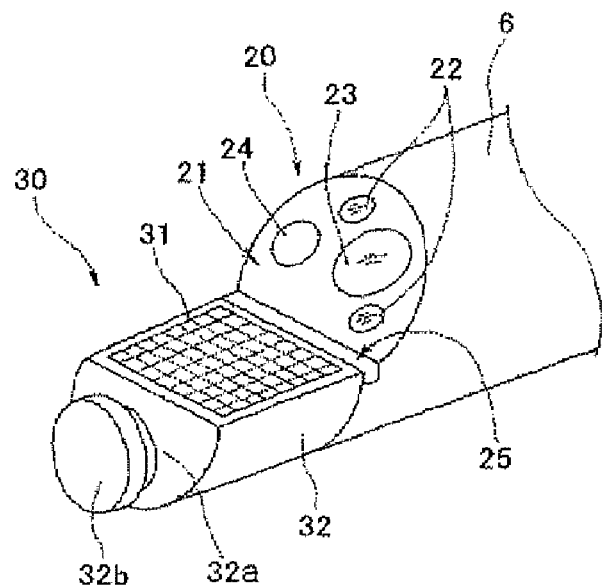
FIG. 3 shows a structure of a distal section of an array type ultrasonic scope according to the first embodiment.

FIG. 3 shows a structure of a distal section of an ultrasonic scope using an array type ultrasonic transducer according to the present embodiment. The distal section 6 is featured with the ultrasonic imaging unit 30 for performing an ultrasound observation. The distal section 6 is also featured with an endoscopic observation part 21.

The endoscopic observation part 21 is equipped with a light guide opening part 22, an image guide opening part 23 and a instrument channel port 24. The image guide opening part 23 constitutes an illumination optics unit for transmitting an illuminating light to an observation region. The instrument channel port 24 is an opening through which a treatment instrument introduced from the instrument channel port 18 protrudes. The distal section 6 is featured with a circumferential balloon groove 25. The balloon groove 25 is for mounting a balloon (not shown in the drawing herein), should it be required, that is freely inflatable and de-inflatable and is made of latex, Teflon (a registered trademark) or other such material having ultrasonic permeability. Incidentally, a pipeline opening (not shown in a drawing herein) is equipped near the balloon groove 25. The pipeline opening is for supplying and exhausting water or the like, which is an ultrasound transmission medium, into and out of the balloon.

Note that the light guide opening part 22 accommodates a light guide fiber (not shown in the drawing herein) for transmitting an illuminating light from the light source part equipped in the endoscopic diagnostic equipment 3. A solid state image pickup element (not shown in the drawing herein) extending a signal cable therefrom is equipped at the image focus position of the image guide opening part 23.

The ultrasonic imaging unit 30 primarily comprises an ultrasonic transducer 31 for transmitting and receiving an ultrasound and a housing 32. The ultrasonic transducer 31 transmits and receives an ultrasound. The housing 32 houses the ultrasonic transducer 31 which is stationarily mounted to the distal section 6.

Note that the distal section of the housing 32 is featured with a salient 32b which has a circumferential balloon groove 32a for mounting a balloon should it be required. Further, the surface of the cMUT 31 and a part of the housing 32 are covered with a protective film formed with parylene (i.e., polyparaxylene), or such, with strong water and chemical resistance.

FIG. 4 shows an external view of a cMUT array type ultrasonic transducer according to the present embodiment. The cMUT 31A shown in FIG. 4 is an enlargement of the cMUT 31 shown in FIG. 3. The cMUT 31A has an array structure as shown in FIG. 4.

The cMUT 31 comprises a plurality of cMUT elements 31a, a cable connector 34 and a signal wire 33. The cMUT element 31a is a cMUT which results from processing a silicon semiconductor substrate by employing a silicon micromachining technique. The cMUT element 31a is produced in a "silicon process" in which products are automatically produced strictly on the basis of the operating sequence in a completely clean environment, while excluding manual work.

The cMUT 31 is formed as an electron sector scanning-use single dimensional array transducer by, for example arraying a plurality of cMUT elements 31a. The individual cMUT elements 31a, constituting the cMUT 31, are configured to be electrically connected to signal wires 33 by way of the cable connector 34.

The signal wires 33 extended from the cable connector 34 are bundled together, extended toward the operation unit 12 in such a state that they are led through a sheath (not shown in a drawing herein) which goes through the insertion tube 11, and are electrically connected to the ultrasonic diagnostic equipment 4.

Figure 5:
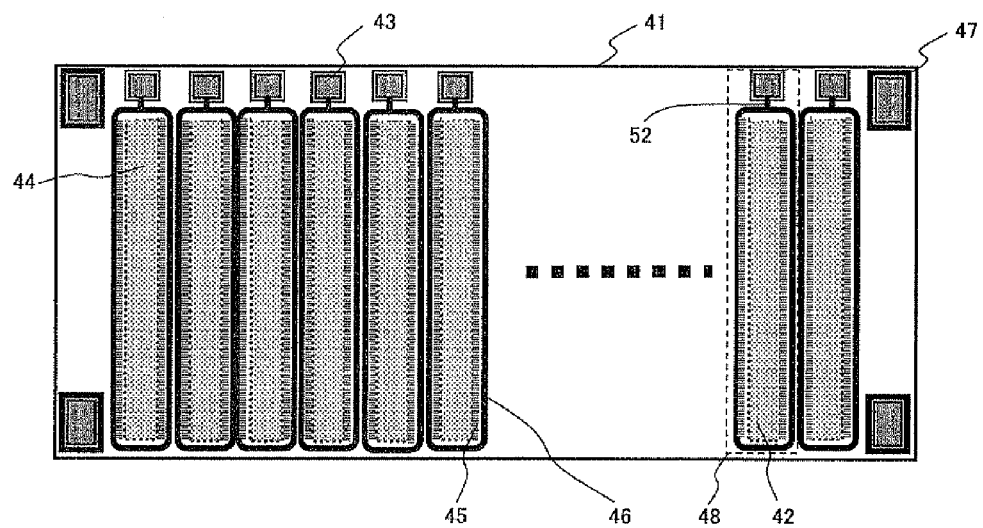
FIG. 5 shows an enlarged diagram of a cMUT array type ultrasonic transducer according to the first embodiment.

FIG. 5 shows an enlarged diagram of a cMUT array type ultrasonic transducer according to the present embodiment. FIG. 5 is an enlargement of a part of the surface of the cMUT 31 shown in FIG. 4. The cMUT array 41 comprises elements constituting an array structure, pads and such, as shown in FIG. 5.

The cMUT 41 is constituted of a plurality of cMUT elements 42, electrode pads for element signal 43 corresponding to the individual cMUT elements 42 and by common ground electrode pads 47. In FIG. 5, the cMUT element 42 is constituted of a plurality of cMUT subelement 44, a common signal interconnect 46 and an inter-subelement-common signal wiring joinder electrode 45.

The common signal interconnect 46 is placed so as to surround the cMUT subelement 44. The electrode for interconnecting from a cell group to common signal line 45 is an electrode for joining a predetermined subelement to a common signal interconnect 46 corresponding to the aforementioned subelement.

Next is a description of the common ground electrode pad 47. The surface of the cMUT is an ultrasound emission surface which is constituted by a membrane film (i.e., layer) which oscillates upon an application of a voltage. One of the constituent components of the membrane is a ground electrode layer which is covered with a protective film, a part of which is equipped with an electrode pad, that is, the common ground electrode pad 47, for being electrically connected to the ground electrode layer.

Figure 6:
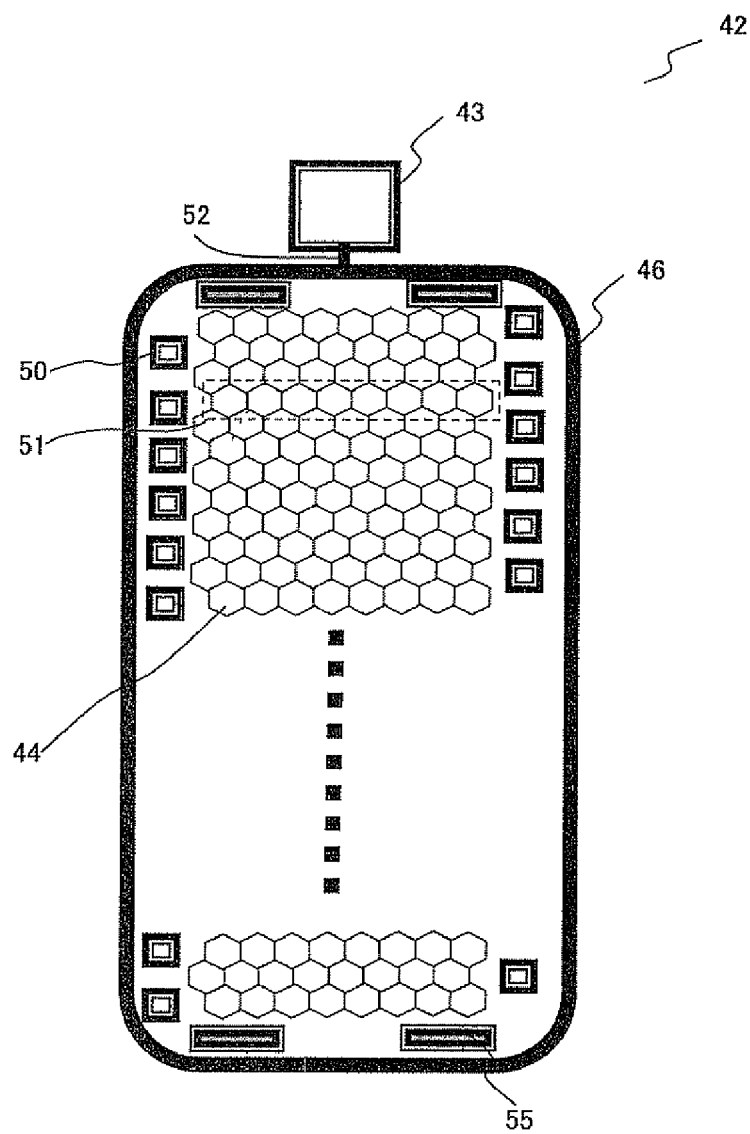
FIG. 6 shows an enlarged diagram of a cMUT element 42 shown in FIG. 5 (before wire-connecting a common signal interconnect 46 to an inter-subelement-common signal wiring joinder interconnect 45)
Figure 7:
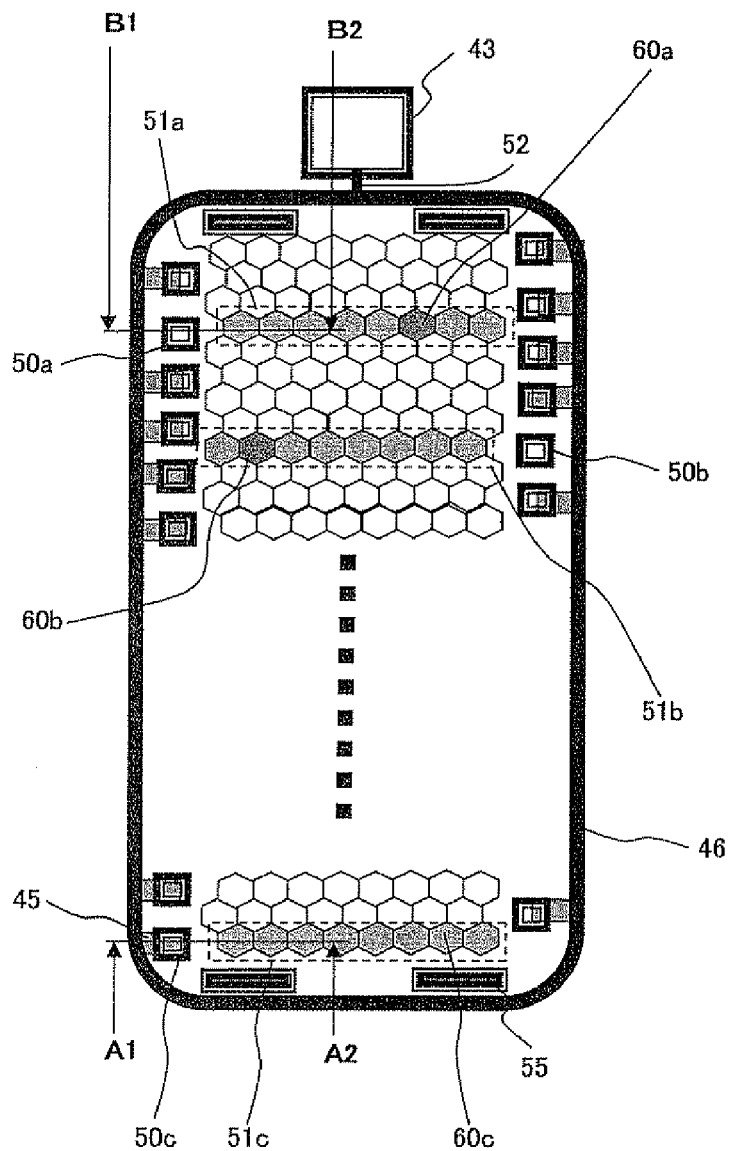
FIG. 7 shows the cMUT element 42 after checking for a defect cell.

FIGS. 6 and 7 show enlargements of the cMUT element 42 and electrode pad for element signal 43 respectively, which are enclosed by the dotted line 48 shown in FIG. 5.

FIG. 6 shows an enlarged diagram of the cMUT element 42 shown in FIG. 5 (before wire-connecting a common signal interconnect 46 to an electrode for interconnecting from a cell group to common signal line 45). Referring to FIG. 6, the individual cMUT cells 44 are hexagonally formed and they are formed in a honeycomb. Four corners of the cMUT elements 44 are equipped with common ground electrode pads 55. The common ground electrode pad 55 is an electrode pad electrically connected to an upper electrode (i.e., a ground-side electrode).

The numeral 51 indicates a cMUT subelement (noted as "subelement" hereinafter) on the same row. A pad for signal in/out 50 is an electrode pad corresponding to the respective subelement 51. The common signal interconnect 46 is connected to the element signal input/output electrodes 43 by way of wiring 52.

Next is a description of the procedure for checking for a defect cell in the cMUT element 42. First is to detect whether or not a failure such as a shorting has occurred to the subelement before wire-connecting the common signal interconnect 46 to the pad for signal in/out 50 (that is, a defect cell check as described in FIG. 1).

In this case, a defect cell check is carried out for the sub-element unit. First a voltage is applied between the pad for signal in/out 50 and the common ground electrode pad 55 and a defect cell check is performed (e.g., a measurement of capacitance and dielectric loss, a measurement of DC resistance, a noncontact infrared temperature inspection and an imaging method by using an electron beam), as described in FIG. 1.

If a defect cell is detected in the defect cell check, a photolithography is applied without wire-connecting the cell (or the subelement) in the wiring process. Alternatively, only a wiring connecting to the cell is cut off by a laser cutter or trimming after finishing all the wiring. This limits damage only to the defect cell (or subelement). The "open" cell is merely inoperable and therefore the damage can be minimized.

FIG. 7 shows the cMUT element 42 after checking for a defect cell. If the subelement (that is, the entirety of cells constituting the subelement) is normal as a result of a defect cell check, the electrode for interconnecting from a cell group to common signal line 45 is provided for wire-connecting a pad for signal in/out corresponding to the subelement to the common signal interconnect 46.

As an example, the entirety of cells 60c within a subelement 51c is normal and therefore a shorting has not occurred, hence there is no problem in the subelement. Therefore, the pad for signal in/out 50c corresponding to the subelement is wire-connected to the common signal interconnect 46.

Contrarily, if a subelement (that is, the entirety of cells constituting the subelement) is abnormal as a result of the defect cell check, a pad for signal in/out 50 corresponding to the subelement is not wire-connected to the common signal interconnect 46.

As an example, a cell 60a in a subelement 51a is shorted, constituting an abnormal (i.e., a failed) cell, and accordingly there is a problem in the subelement. Therefore, a pad for signal in/out 50a corresponding to the subelement 51a is not wire-connected to the common signal interconnect 46. Likewise for the subelement 51b, there is a defect cell 60b in the subelement 51b and therefore a pad for signal in/out 50b corresponding to the subelement 51b is not wire-connected to the common signal interconnect 46.

Figures 8A, 8B:
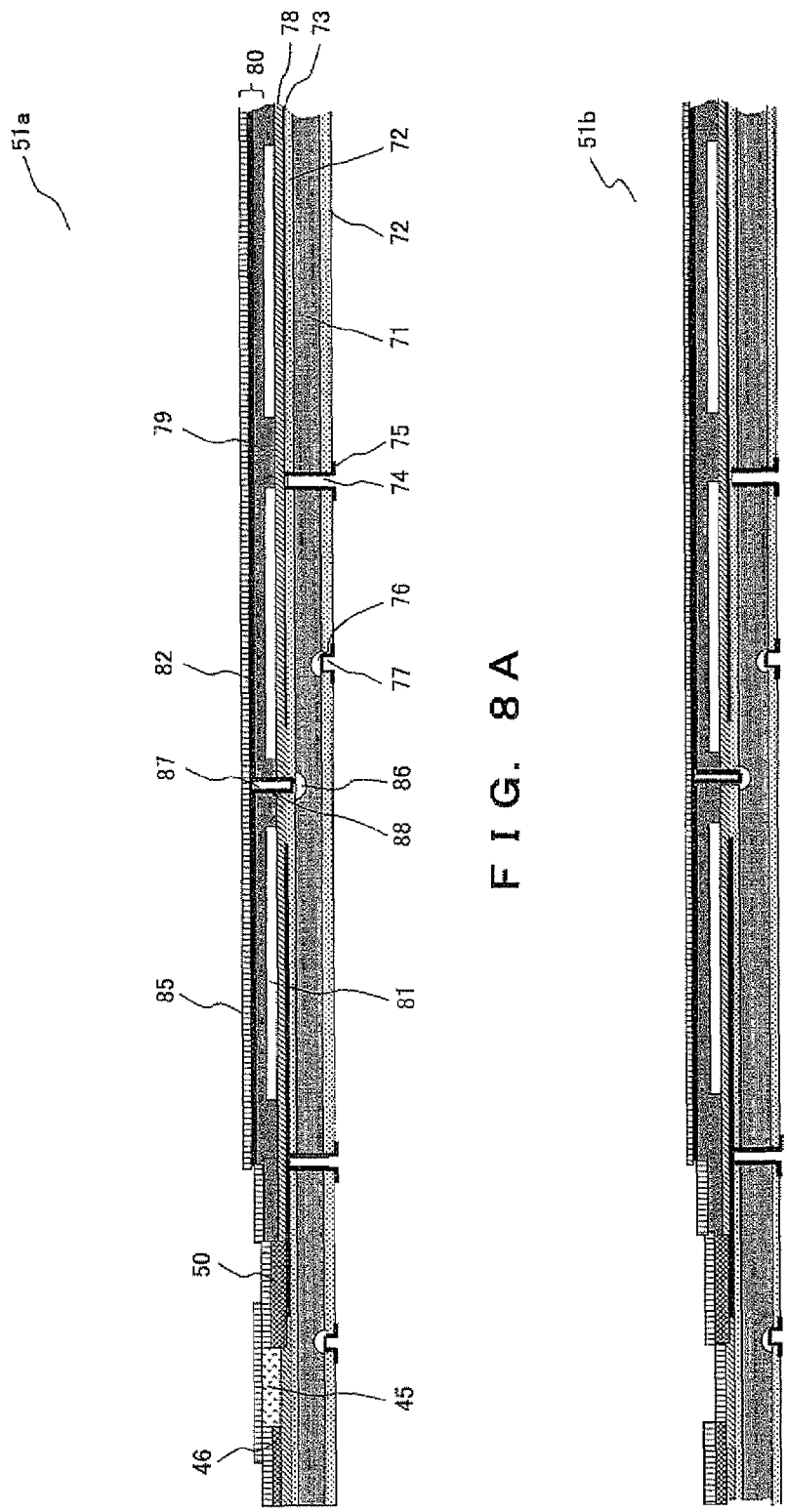
FIG. 8A shows a cross-section of A1-A2 as indicated in FIG. 7.
FIG. 8B shows a cross-section of B1-B2 as indicated in FIG. 7.

FIGS. 8A and 8B show cross-sectional view of FIG. 7. FIG. 8A shows the cross-section A1-A2 of FIG. 7. Referring to FIG. 8A, a cMUT element (i.e., a subelement 51a herein) comprises a silicon substrate 71, a surface oxide film 72, a bottom electrode (i.e., a signal in/out electrode) 73, a via through substrate 74, an electrode pad 75, an diffusion region for ohmic contact 76, a electrode pad for ground 77, a dielectric film 78, a membrane supporting part 79, a membrane 80, a cavity 81, an upper electrode 82, a pad for signal in/out 50, a common signal interconnect 46, a protective film 85, an diffusion region for ohmic contact 86, a via 87 and a via conductor (i.e., a ground side) 88.

The membrane 80 is a vibrating film fixed by the membrane supporting part 79 at the edge. The membrane 80 is constituted of a plurality of membrane films in terms of the production process. One of the constituent components of the membrane 80 includes the upper electrode 82. In the configuration of FIG. 8A, the protective film 85 is formed on the surface of the upper electrode 82.

The oxide film (made of $SiO_2$) 72 is formed on the surfaces (i.e., the front and back surfaces) of the silicon substrate 71. The bottom electrode 73 is formed on the oxide film on the silicon substrate 71. The dielectric film (e.g., $SiO_2$) 78 is formed on the bottom electrode 73. Note that the dielectric film 78 may use a material having a high dielectric constant such as SiN, barium titanate $BaTiO_3$, barium-strontium titanate, tantalum pentoxide, niobium oxide-stabilized tantalum pentoxide, aluminum oxide or titanium oxide $TiO_2$, in lieu of being limited to $SrTiO_3$.

The electrode pad 75 equipped on the back surface of the silicon substrate 32 is an electrode pad used for the bottom electrode which is connected from the bottom electrode 73 via the wiring (i.e., the wiring featured on the inside wall of the via through substrate 74) formed in the via through substrate 74. The electrode pad 75 is a terminal for receiving an input of a drive signal for driving the cMUT at the time of transmitting an ultrasound and for outputting an ultrasonic echo signal to the ultrasonic diagnostic equipment at the time of receiving an ultrasound. The present embodiment, however, is configured to input and output a signal to and from the pad for signal in/out 50 instead of the terminal.

The upper electrode 82 has an electrical continuity to the via conductor 88 of the via 87. The electrode pad for ground 77 is a pad for conducting the via conductor 88 formed on the surface of the inside of the via 87 to the back surface of the silicon substrate (i.e., a low resistance silicon substrate) 71 in order to connect the upper electrode 82 to the ground (GND). This makes it possible to use the pad 77 as a common ground electrode.

The dielectric film 78 is for increasing capacitance across the upper electrode 82 and bottom electrode 73 which sandwich the cavity 81. The diffusion regions for ohmic contact 76 and 86 are for forming an electrical continuity path for leading the silicon substrate 71 to the rear side of the silicon substrate 71 as a ground channel in a zone for decreasing the contact resistance between the ground electrode and substrate without allowing it to have a property of rectification.

The silicon substrate 71 is structured so as to minimize the contact resistance between the electrode pad for ground 77 and the via conductor 88 placed on the bottom part of the via 87.

The pad for signal in/out 50 is equipped on the upper surface of the bottom electrode 73 shown on the left side of FIG. 8A. The common signal interconnect 46 is equipped near and distanced from the pad for signal in/out 50 by the insulation zone. Also, the pad for signal in/out 50 has an electrical continuity to the common signal interconnect 46 by way of the electrode for interconnecting from a subelement to common signal line 45.

Note that, referring to FIG. 8A, the second and third cMUT cells from the left are connected to the bottom electrode 73 while the first seems to be independent thereof; however, in actuality, the bottom electrode 73 is connected in a manner so as to avoid the diffusion region for ohmic contact 86 and via conductor (on the signal side) 88.

FIG. 8B shows a cross-section of B1-B2 indicated in FIG. 7. FIG. 8B is a cross-section corresponding to the subelement 51*b* shown in FIG. 7. Differing from FIG. 8A, there is no electrode for interconnecting from a subelement to common signal line 45. Therefore, the pad for signal in/out 50 has no electrical continuity to the common signal interconnect 46.

As an example, if an abnormality such as a shorting is discovered in the rightmost cell among the three cells shown in FIG. 8B, a wire-connection between the pad for signal in/out 50 and the common signal interconnect 46 by using the electrode for interconnecting from a subelement to common signal line 45 is not carried out.

Note that the electrode pad 75 is not used for inputting or outputting a signal to or from the pad for signal in/out 50 as described above.

In actuality, however, there is a need for provisions such as a pulser (to be described later), a charge amplifier (to be described later) and a control circuit such as a switch circuit just under the cMUT element, and therefore an electrode pad is formed on the rear side, followed by connecting a minute control circuit by using a solder bump or such.

Note that a defect cell check by the subelement unit has been described in FIGS. 6 and 7; it is, however, possible to carry out a defect cell check by the element. Referring to FIG. 5, as an example, it is possible to carry out a defect cell check by employing a method using an SEM or an EBIC method by applying a voltage between the element signal input/output electrodes 43 and the common ground electrode pad 47. In this case, the wiring 52 needs to be unconnected; if the wiring 52 is already connected, however, it is possible to apply a later described third embodiment.

As described above, the cMUT according to the present invention is contrived to integrate a plurality of cMUT cells, each of which comprises a bottom electrode formed on a silicon substrate; a support part which is placed on the silicon substrate and which supports a membrane; and a membrane (including an upper electrode) which constitutes a sound source for transmitting an ultrasound as a result of vibrantly displacing itself. It is also configured to mutually wire-connect bottom electrodes in parallel and to mutually wire-connect upper electrodes in parallel for each specific integrated subelement, and to comprise at least one check-use electrode pad at a part of the wiring or at an extended wiring therefrom.

Also, the cMUT according to the present invention comprising a plurality of integrated subelements and check-use electrode pads corresponding to the integrated subelements is contrived in a manner such that the wiring for connecting to a common signal wiring has an electrical continuity only to a check-use electrode pad accompanying an integrated subelement in which a defect check has confirmed no occurrence of abnormality.

The present invention is also contrived to place a check-use electrode pad on the same side as a ground electrode pad. Furthermore, the surface featured with the check-use electrode pad and ground electrode pad is on the side for transmitting and receiving an ultrasound. This contrivance is beneficial for the following reason. Whether or not wire-connect a common signal wiring to a signal in/out pad is determined after performing a confirmation check of an abnormality occurrence situation. This check is a process check and therefore, if the ground electrode pad and signal electrode pad are on a different surface or on a rear surface, it is cumbersome to touch them with respective probes; the contrivance of the present invention, however, eliminates such cumbersomeness.

The present invention is also contrived to enable a failure check of an integrated subelement (or cell or element) by measuring the capacitance and dielectric loss. It is also contrived to enable a failure check of an integrated subelement (or cell or element) by applying a DC bias and measuring the capacitance and dielectric loss. It is also contrived to enable a failure check of an integrated subelement (or cell or element) by measuring the DC resistance. It is also contrived to enable a failure check of an integrated subelement (or cell or element) by performing a noncontact infrared thermal inspection. A failure check of an integrated subelement (or cell or element) may employ an imaging method using an electron beam.

Note that the imaging method using an electron beam may employ either the voltage contrast imaging (VCI) method, specimen absorbed current (SAC) method, resistance contrast imaging (RCI) method, or electron beam induced current (EBIC) method, or an inspection method combining some of the aforementioned methods.

As such, it is possible to make a defect cell detected by a defect cell check simply inoperable and therefore to suppress damage to a normal element, thereby preventing the entirety of the element or the entirety of the ultrasonic transducer from shorting and thus becoming inoperable.

Also, the contrivance of placing the ground electrode pad and signal in/out electrode pad on the same surface (i.e., an ultrasound emission surface) makes the defect cell check easy.

Second Embodiment

While the first embodiment has been described on the cMUT element arraying a subelement in one direction; the present embodiment is described on a different aspect of a cMUT element or array. Note that, except for the configuration of a cMUT element or cMUT array, the configuration is similar to that of the first embodiment.

Figure 9:
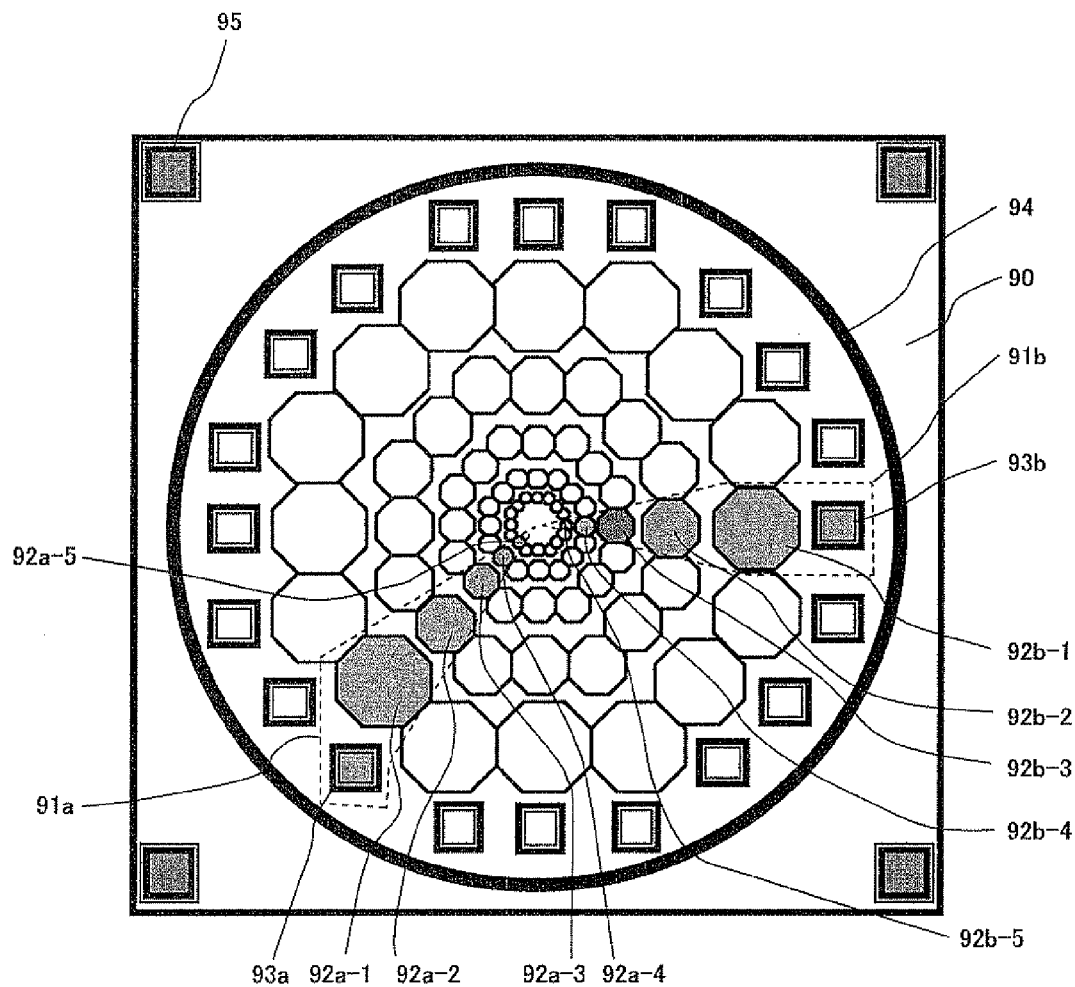
FIG. 9 exemplifies a cMUT element before wire-connecting a signal electrode pad interconnected from cell group to a common signal wiring according to the second embodiment.

FIG. 9 exemplifies a cMUT element before wire-connecting a signal electrode pad interconnected from subelement to a common signal wiring according to the present embodiment. FIG. 9 shows a cMUT element arraying subelements in an approximate concentricity, in which a signal electrode pad interconnected from subelement is not yet wire-connected to a common signal wiring. A cMUT 90 is a cMUT of a circular opening form. The cMUT 90 is configured to array subelements 92 (i.e., 92a-1, 92a-2, 92a-3, 92a-4, 92a-5, 92b-1, 92b-2, 92b-3, 92b-4, 92b-5 and so on) approximately concentrically.

Here, the present embodiment is configured such that the subelements exist in radial directions. As an example, the subelement 91a is constituted of cells, i.e., 92a-1, 92a-2, 92a-3, 92a-4 and 92a-5, which are arrayed from the edge of a circular form across to the center. The area size of a cell increases toward the circumference. A signal electrode pad interconnected from subelement 93a corresponding to the subelement 91a is equipped near the cell 92a-1 existing at the outermost position of the subelement 91a.

A signal electrode pad interconnected from subelement corresponding to an individual subelement 91 is indicated by the numeral 93 in the following description.

The subelement 91b is constituted of cells, i.e., 92b-1, 92b-2, 92b-3, 92b-4 and 92b-5, which are arrayed from the edge of a circular form across to the center. A signal electrode pad interconnected from subelement 93b corresponding to the subelement 91b is equipped near the cell 92b-1 existing at the outermost position of the subelement 91b. Here, the assumption is that the cell 92b-3 of the subelement 91b is a defect cell.

Other subelements are normal subelements similar to the subelement 91a. These subelements are surrounded by a circular common signal interconnect 94. Common ground electrode pads 95 are respectively equipped on the four corners of the cMUT element 90. The common ground electrode pad 95 is an electrode pad having an electrical continuity to an upper electrode (i.e., a ground electrode).

In this case, a defect cell check is carried out by the subelement unit. First is to apply a voltage between the signal electrode pad interconnected from subelement 93 and the common ground electrode pad 95 and perform a defect cell check (e.g., a measurement of the capacitance and dielectric loss, a measurement of the DC resistance, a noncontact infrared temperature inspection, and an imaging method using an electron beam).

FIG. 10 exemplifies a cMUT element after wire-connecting a signal electrode pad interconnected from subelement to a common signal wiring according to the present embodiment. FIG. 10 is a description after wire-connecting the signal electrode pad interconnected from subelement and common signal wiring except for the defect subelement shown in FIG. 9.

If a subelement (that is, the entirety of cells constituting the subelement) is found to be normal in the defect cell check, an electrode for interconnecting from a subelement to common signal line 100 is provided in order to wire-connect a signal electrode pad interconnected from subelement 93 to a common signal interconnect 94 corresponding to the subelement. As an example, the cells 92a-1, 92a-2, 92a-3, 92a-4, 92a-5 within the subelement 91a are all normal, making the subelement normal. Therefore, the signal electrode pad interconnected from subelement 93a and common signal interconnect 94 corresponding to the subelement 91a are wire-connected together by using the inter-subelement-common signal wiring joinder electrode 100.

Contrarily, if a subelement (that is, the entirety of cells constituting the subelement) is found to be abnormal in the defect cell check, a signal electrode pad interconnected from subelement corresponding to the subelement is not wire-connected to the common signal interconnect 94. As an example, the cell 92b-3 within the subelement 91b is abnormal (i.e., a defect cell), making the subelement also problematic. Therefore, the signal electrode pad interconnected from subelement 93b corresponding to the subelement 91b is not wire-connected to the common signal interconnect 94. Because other subelements are normal like the subelement 91a, the signal electrode pads interconnected from subelement corresponding to respective subelements are wire-connected to the common signal wiring via the inter-subelement-common signal wiring joinder electrode 100.

FIG. 11 exemplifies another cMUT element before wire-connecting a signal electrode pad interconnected from sub-element to a common signal wiring according to the present embodiment. Note that the present embodiment eventually aims at forming a cMUT transducer of a two-terminal structure, and therefore the expression of "element" may be directly replaced with an expression of transducer, as is also the case with FIG. 14 which is described later.

A cMUT chip 110 is primarily constituted of eight zones as a result of dividing a circle into eight equal parts. These eight zones are separated by boundary regions 112. Then, each of the eight zones are further constituted of three zones 111, 116 and 118 (FIG. 11 shows the divided zones of a transducer element in the radial direction divided by the border lines 117). The three individual zones 111, 116 and 118 are transducer element A, transducer element B and transducer element C, respectively. This makes for a total of twenty-four transducer elements.

The numeral 113 is a common signal wiring for the transducer element A (111). The numeral 114 is a common signal wiring for the transducer element B (116). The numeral 119 is a common signal wiring for the transducer cell group C (118).

The numeral 122 is a common electrode pad for signal in/out for the transducer element A (111). The numeral 121 is a common electrode pad for signal in/out for the transducer element B (116). The numeral 120 is a common electrode pad for signal in/out for the transducer element C (119).

The common electrode pad for signal in/out 122 has an electrical continuity to the common signal interconnect 113. The common electrode pad for signal in/out 121 has an electrical continuity to the common signal interconnect 114. The common electrode pad for signal in/out 120 has an electrical continuity to the common signal interconnect 119.

As such, the common signal wiring of each transducer element has an electrical continuity to the corresponding common electrode pads for signal in/out 122. Note that the wiring connecting the common signal wiring to the common electrode pad for signal in/out has an electrical continuity to the bottom electrode and is buried in the silicon substrate and therefore is actually invisible from the outside (N.B.: FIG. 1 is delineated as if it is on the membrane surface, which is just for convenience of description).

The numeral 123 is a common pad for connection which corresponds to the common signal interconnect 46 shown in FIG. 6. Common ground electrode pads 124 are respectively equipped on the four corners of the cMUT chip 110. The common ground electrode pad 124 is an electrode pad having an electrical continuity to the upper electrode (i.e., the ground side electrode).

Figure 12:
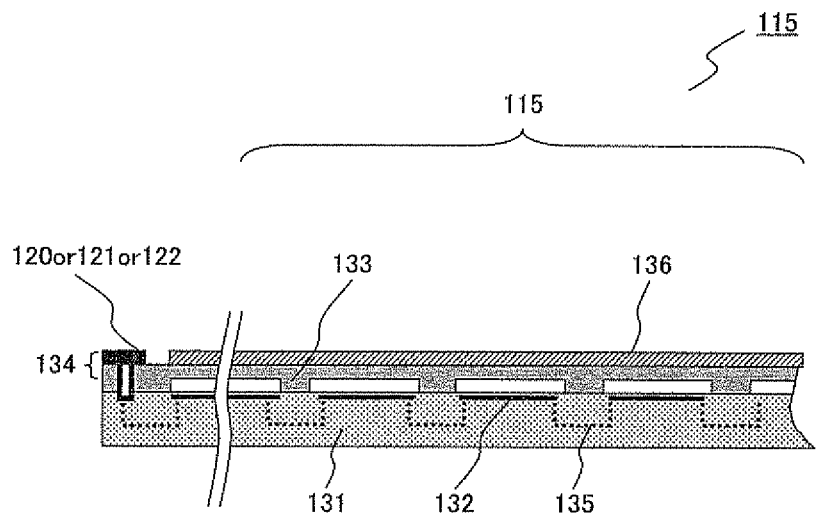
FIG. 12 shows an illustration diagram of a cross-section of a zone 115 of a part of a transducer cell group shown in FIG. 11.

FIG. 12 shows an illustration diagram of a cross-section of a zone 115 of a part of the transducer element shown in FIG. 11. A group of transducer cells 115 comprises a silicon substrate 131, a bottom electrode 132, a membrane supporting part 133, a membrane 134 (including an upper electrode 136) and interconnects connected among bottom electrodes 135.

The interconnects connected among bottom electrodes 135 mutually connects bottom electrodes electrically. Other configurations are basically similar to the one described in FIG. 8. Note that the leftmost part of FIG. 12 is a cross-section of the common electrode pad for signal in/out 120, 121 or 122.

Figure 13:
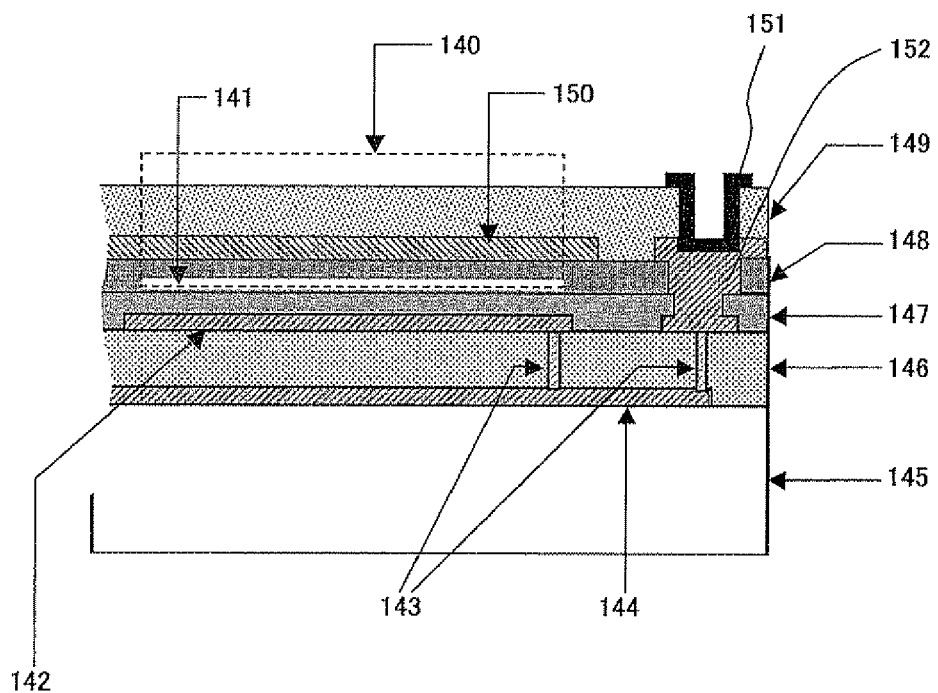
FIG. 13 shows a detailed configuration of FIG. 12.

FIG. 13 shows a detailed configuration of FIG. 12. The cMUT according to the present embodiment comprises a substrate ((made from) Si or glass) 145, a first insulation layer (SiN) 146, a second insulation layer ($Ta_2O_5$) 147, a third insulation layer (SiN) 148, a protective film (SiN) 149, a bottom electrode (Ta) 142, a first electrode 144, a contact via 143, an upper electrode (Al) 150 and a common electrode pad for signal in/out 151. The common electrode pad for signal in/out 151 corresponds to the common electrode pads for signal in/out 120, 121 and 122.

The first electrode 144 is formed on the substrate (Si or glass) 145. The first insulation layer 146 is formed on the first electrode 144. The bottom electrode 142 is formed on the first insulation layer 146. The second insulation layer 147 is formed on the bottom electrode 142. The third insulation layer 148 is formed on the second insulation layer 147.

A cavity (i.e., an air or vacuum part) 141 is formed in the third insulation layer 148. The upper electrode 150 is formed on the third insulation layer 148. The protective film 149 is formed on the upper electrode 150.

The membrane 140 is constituted of the third insulation layer 148, upper electrode 150 and protective film 149. The rightmost part of the cMUT shown in FIG. 13 is equipped with the common electrode pad for signal in/out 151 penetrating the protective film 149. A conductive via 152 is formed as to interconnect a contact via 143 and the common electrode pad for signal in/out pad 151. The conductive via 152 has an electrical continuity to the first electrode 144 by way of the contact via 143. Also, the bottom electrode 142 has an electrical continuity to the first electrode 144 by way of the contact via 143.

The following describes the procedure for a defect cell check for the cMUT shown in FIG. 11. In this case, the defect cell check is carried out by the transducer element unit (e.g., the transducer element A, transducer element B and transducer element C). The first step is to apply a voltage between the common electrode pad for signal in/out (120, 121 or 122) and common ground electrode pad 124 and the defect cell check is carried out as in the case of the first embodiment.

Figure 14:
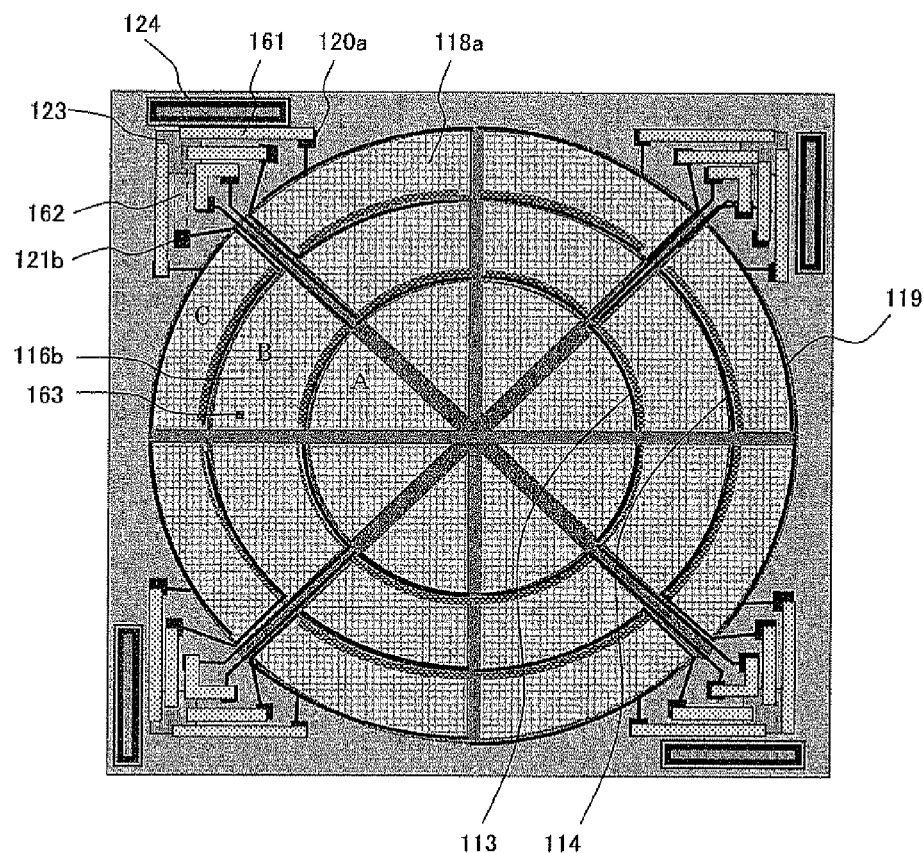
FIG. 14 exemplifies another cMUT element after wire-connecting signal electrode pads interconnected from cell group to common signal wirings according to the second embodiment.

FIG. 14 exemplifies another cMUT element after wire-connecting signal electrode pads interconnected from element to common signal wirings according to the present cell group embodiment. FIG. 14 shows the configuration after wire-connecting the signal electrode pads interconnected from element to common signal wirings except for a defect element in the configuration of FIG. 12.

The common signal wirings 113, 114 and 119 are provided for the respective units of the transducer element A, B, C, and therefore, if there is a defect cell in a part of the individual transducer, the entirety of the transducer element needs to be isolated from a common signal wiring because it is impossible to cause only the failed part to not be connected to a common signal wiring. This is the reason for carrying out a defect cell check by the transducer element unit. Therefore, if there is a defect cell in a part of a transducer element, the transducer element per se is handled as a failure.

As an example, if a cell 163 of a part of the transducer element B (116b) fails, the transducer element B (116b) is handled as a failure. Accordingly, the common electrode pad for signal in/out 121b of the transducer element B (116b) is not wire-connected to the common pad for connection 123 (N.B.: the dotted line of the numeral 162 indicates the situation in which the common electrode pad for signal in/out 121b is not wire-connected to the common pad for connection 123).

In contrast, a defect cell does not exist within the transducer element C (118a), and therefore the common electrode pad for signal in/out 120a of the transducer element C (118a) is wire-connected to the common pad for connection 123 via an interconnect between common signal in/out pads 161.

Meanwhile, whether or not to wire-connect between a common signal wiring and a signal input/output electrode pad is determined after a confirmation check of an abnormal occurrence situation. Since the confirmation check is a process check, the existence of the ground electrode pad and signal input/output electrode pad on a single surface or both surfaces makes the check easy. The use of the defect cell check according to the present embodiment applies various cMUT's shape.

Third Embodiment

The first and second embodiments detect whether or not a failure such as a shorting has occurred in a subelement before wire-connecting the common signal interconnect 46 to a pad for signal in/out 50 in the configuration of FIG. 6, for example. Comparably, the present embodiment is configured to detect whether or not a failure has occurred in the state of the common signal interconnect 46 and the pad for signal in/out 50 which has already been wire-connected.

Figure 15:
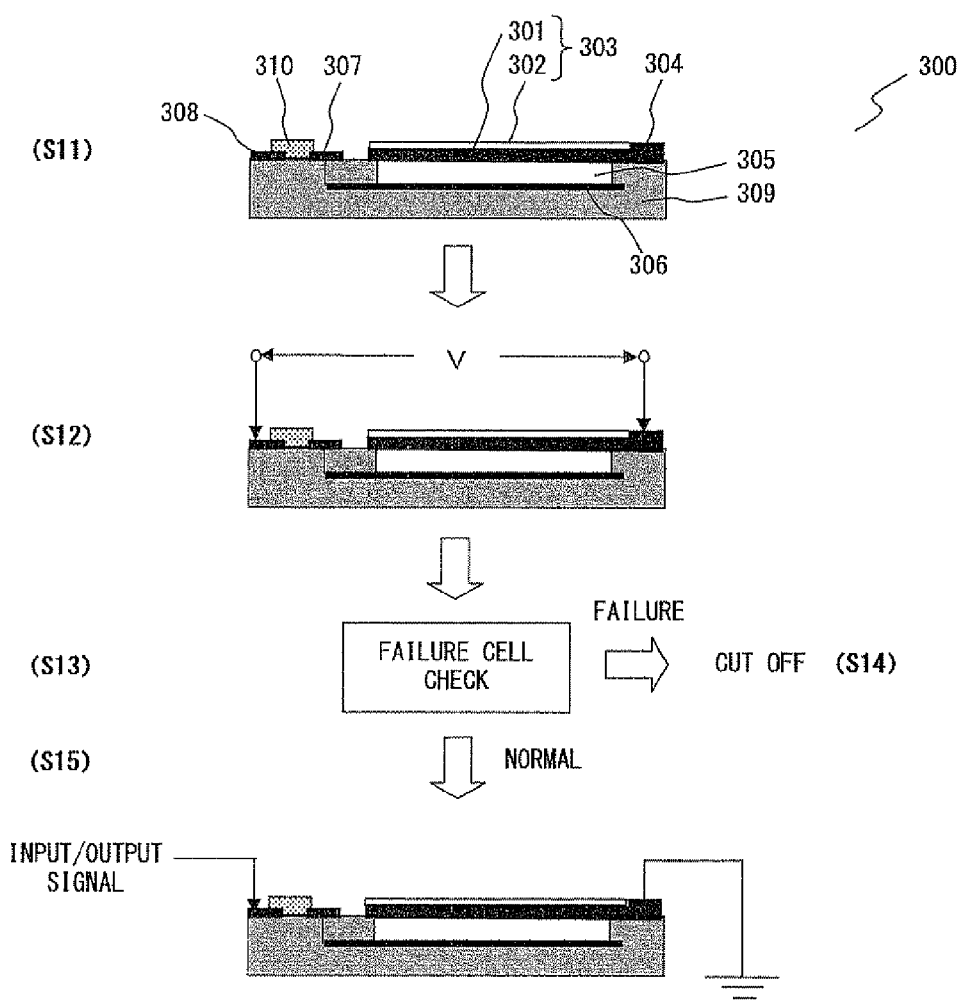
FIG. 15 is a conceptual diagram of a defect cell check of a cMUT element according to the third embodiment.

FIG. 15 is a conceptual diagram of a defect cell check of a cMUT element according to the present embodiment. The first step is to form cells in a process before completing a cMUT element, equip each cell (or element) with a signal in/out electrode pad, and connect all the signal in/out electrode pads to the common signal wirings (S11).

The S11 is the state of wire-connecting signal electrode pads 307 of all cells to common signal wirings 308 by way of an interconnect combining cells and common signal 310 without performing a defect cell check (S11 and S12) in the process of FIG. 1.

Next is to perform a defect cell check for each cell (or cell group) (S12 and S13). In the defect cell check of the present embodiment, it is detected whether or not a defect such as a shorting has occurred in any of the cells in the state of the signal electrode pads 307 which are wire-connected to the common signal wirings 308.

In the present embodiment, the noncontact infrared thermal inspection and imaging method by using an electron beam are effective methods from among the methods for a defect cell check as described in FIG. 1. In the case of a defect cell check by the noncontact infrared thermal inspection for example, the first step is to apply a voltage between the common signal interconnect 308 and the common ground electrode pad 304 in order to apply a voltage between the upper electrode 301 and bottom electrode 306 (S12). In this event, if there is a spot of a shorting between the upper electrode 301 and bottom electrode 306, the application of a voltage causes the shorted spot to heat up or light up.

Therefore, a defect cell can be detected by applying a voltage between the common signal wirings 308 and the common ground electrode pad 304 and by examining a spot of heating up or radiating on the element by using an infrared sensor with a microscope function (e.g., a thermo viewer) (S13).

Alternately, in the case of a defect cell check by an imaging method using an electron beam, an application of a predetermined potential between the common signal interconnect 308 and common ground electrode pad 304, for example, followed by a detection by employing the EBIC method, obtains an electronic image in which only the spot of shorting has a different brightness, enabling a detection of a defect spot.

If a defect cell is detected (a shorted cell part glows faintly) as a result of the defect cell check, only an interconnect combining cells and common signal 310 corresponding to the glowing cell is cut off by using a laser cutter or such (S14).

As described above, such a glow can be observed with a microscope and therefore the process is easily applicable to a laser cutter using a microscope system. Also, a flow of electric current causes the shorted spot to heat up, making it possible to detect a defect cell by measuring temperature or observing infrared radiation.

Figure 16:
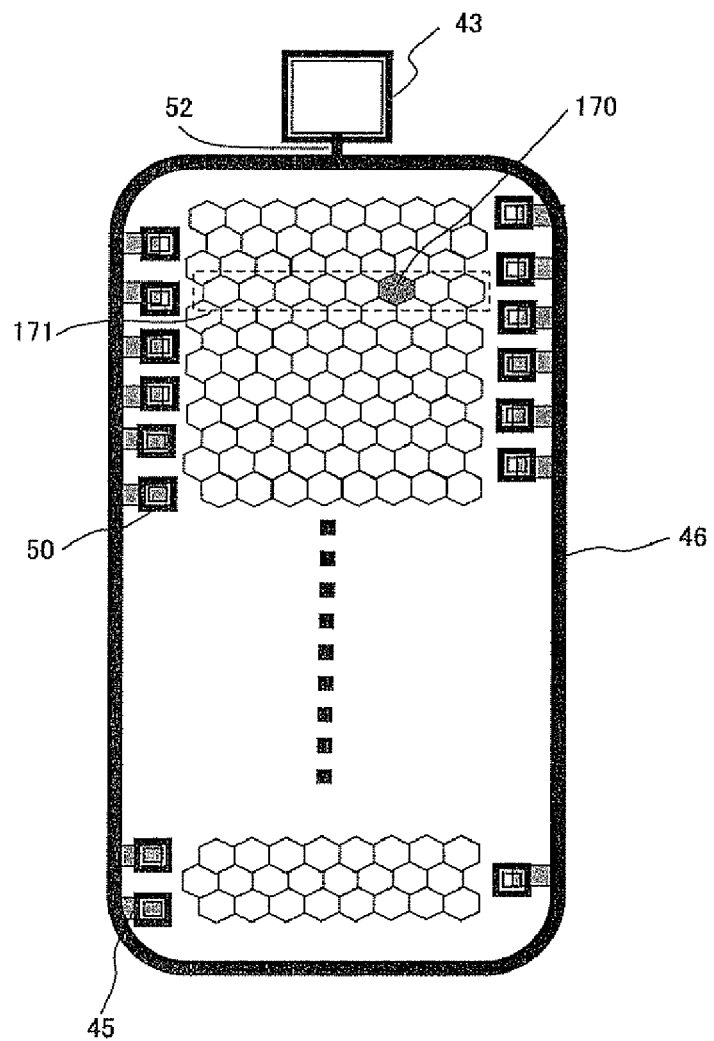
FIG. 16 shows a state in which all common signal wirings 46 are already wire-connected to electrodes for interconnecting from a cell group to common signal line 45 on a cMUT element according to the third embodiment.

FIG. 16 shows a state in which all common signal wirings 46 are already wire-connected to electrodes for interconnecting from a cell group to common signal line 45 on a cMUT element according to the present embodiment. FIG. 16 shows the state in which the common signal wirings 46 are already wire-connected to all of the pads for signal in/out 50 by way of the electrode for interconnecting from a cell group to common signal line 45. An application of a predetermined voltage to the silicon substrate in this state, followed by employing the EBIC method, makes it possible to detect a failed spot as a result of only the shorted spot having a different brightness.

Figure 17:
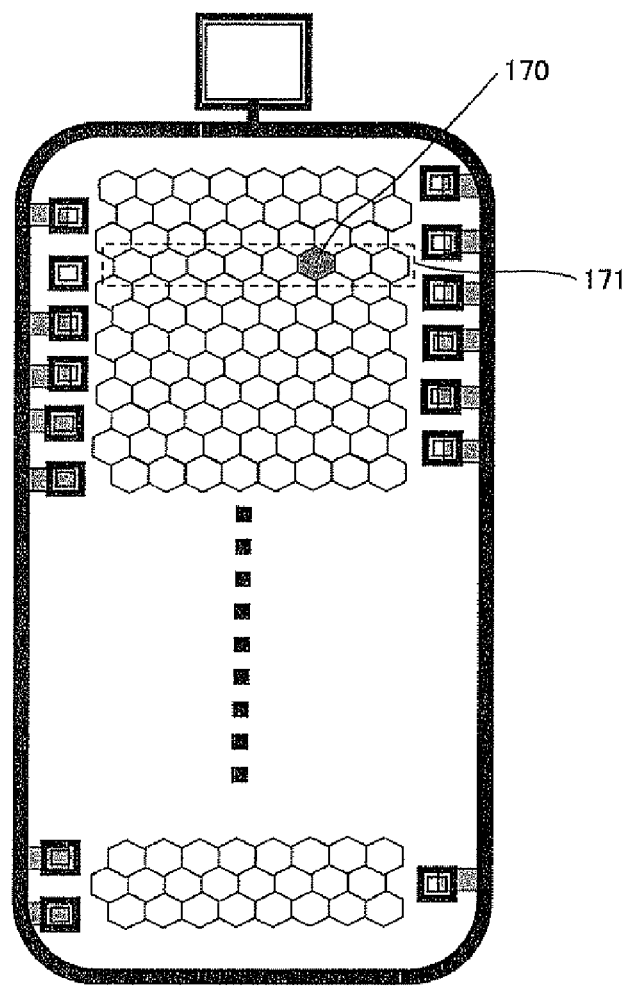
FIG. 17 shows a state in which the electrode for interconnecting from a cell group to common signal line 45 of a defect subelement is cut off according to the third embodiment.

FIG. 17 shows a state in which the electrode for interconnecting from a cell group to common signal line 45 of a defect subelement is cut off according to the present embodiment. FIG. 17 shows the state in which an electrode for interconnecting from a cell group to common signal line 45 corresponding to an applicable subelement 171 is cut off by using a laser cutter because a defect cell check has detected a defect cell 170.

Note that the defect cell check according to the present embodiment is applicable to all of the cMUT (cells, subelement and elements) used for the first and second embodiments.

As described above, the present invention is contrived to carry out the process of forming a wire connection for connecting to the common wiring before the process of checking an integrated subelement by way of the check-use electrode pad.

As such, whether or not a failure has occurred can be detected in the state in which the common signal interconnect 46 is already wire-connected to the pad for signal in/out 50, thereby improving the freedom of the production process of the cMUT. A parallel use with the failure check of the first embodiment is possible, providing an expectation for further quality improvement.

Fourth Embodiment

If a connection related to a defect element is avoided in the cMUT according to the first through third embodiments, an ultrasound reception signal from the defect element is not transmitted to the ultrasonic diagnostic equipment because a transducer element is the unit of drive control. Therefore an ultrasound image corresponding to the ultrasonic reception signal is not obtained. Accordingly, the present embodiment is configured to interpolate for a missing ultrasonic echo signal by using a pseudo signal in place of the missing ultrasonic echo signal.

FIG. 18 shows an illustration diagram of an intra-body tissue ultrasonic diagnosis apparatus comprising an interpolation signal process circuit for interpolating for a missing ultrasonic echo signal among ultrasonic echo signals output from a transducer element according to the present embodiment. The intra-body tissue ultrasonic diagnosis apparatus comprises a cMUT element 201, a pulser 202, a charge amplifier 203, an analog/digital (A/D) converter 204, a pseudo signal generator 205, and an imaging unit 207.

At least the pulser 202 and charge amplifier 203 are equipped for each cMUT element. The pulser 202 and charge amplifier 203 are integrated close to the cMUT element 202, or preferably, on or inside of a silicon substrate forming preferably the cMUT element 201. The A/D conversion circuit 204 is also preferably formed close to the cMUT element 201 or preferably inside of the silicon substrate forming the cMUT element 201; however, it may be featured on the observation apparatus side, in lieu of being limited to the aforementioned configuration.

The analog/digital (A/D) converter 205 is one of the constituent components of a signal process unit (not shown in the drawing herein) of the observation apparatus side. The pseudo signal generator 205 comprises a position detector 205a and a data interpolation unit 205b. A signal process unit applies various signal processes to an input electric signal and generates a video image signal used for an ultrasonic tomography image. The pseudo signal generator 205 according to the present embodiment carries out one of the signal processes, however. In the signal process unit, various signal processes are carried out, including the process at the pseudo signal generator 205, and an ultrasonic tomography image signal is built up at the imaging unit 207. The ultrasonic tomography image signal is output to the monitor 208 in which an ultrasonic tomography image is displayed.

The N pieces of cMUT elements 202 are equipped in the configuration of FIG. 18. The pulser 202 is a pulser circuit for generating an electric signal for driving the cMUT element.

An ultrasonic echo signal received by the cMUT element is output to the charge amplifier 203.

The charge amplifier 203 comprises the function of performing an impedance conversion (converting from high impedance to low impedance), that of detecting a charge on the electrode of the cMUT element and that of an amplifier. The function of detecting a charge is defined as that of detecting a charge because a membrane of the cMUT element 201 vibrates in accordance with the intensity of an echo signal when the cMUT element 201 receives the echo signal.

A converted electric signal of an ultrasonic echo signal from the charge amplifier 203 is converted from the analog signal into a digital signal at the A/D conversion circuit 204. The ultrasonic echo signal converted into the digital signal is input into the pseudo signal generator 205.

At the pseudo signal generator 205, the position detector 205a receives the ultrasonic echo signal from an individual cMUT element 201. The position detector 205a comprises a storage function for temporarily storing a signal and a position detection data for detecting a position of a cMUT corresponding to the received ultrasonic echo signal (or an ultrasonic echo signal could not be received).

Next is a description of the storage function of the position detector 205a. There is a time difference in an output timing of ultrasonic echo signals output from the individual cMUT elements for scanning. In order to perform an interpolation calculation at the data interpolation process unit 205b, it is necessary to generate interpolation data between ultrasound signals when scanning at the same time, however. For this reason, it is necessary to temporarily store the ultrasonic echo signals output from the respective cMUT elements 201 and perform a interpolation algorithm operation process simultaneously in the form of a synchronous time phase. Therefore, the position detector 205a stores ultrasonic echo signals temporarily until the time phases thereof become synchronous with one another.

Next is a description of the position detection function of the position detector 205a. The signal wire described in FIG. 4 is connected to a cMUT element one by one so that the ultrasonic echo signal transmitted in the signal wire can be identified relative to which cMUT element the signal corresponds to.

Therefore, if there is a signal wire to which an ultrasonic echo signal is not input, a cMUT corresponding to the signal wire can be discerned. Also the data interpolation process unit 205b pre-stores position information of the cMUT element (e.g., if transducer elements are arrayed in an ultrasonic transducer in a matrix, the coordinates of the transducer elements). This configuration makes it possible to obtain the position information of the specific cMUT element.

The position detection function enables the position detector 205a to recognize the position information of a cMUT element 201 corresponding to each ultrasonic echo signal. Therefore, it is also enabled the recognition of an adjoining relationship of the cMUT elements corresponding to individual ultrasonic echo signals.

In contrast, if an ultrasonic echo signal is not input in the meantime, the position of a cMUT element corresponding to an ultrasonic echo signal, which should have been input, can be identified. This accordingly makes it possible to identify the position of a defect element.

The ultrasonic echo signals output from the position detector 205a are input into the data interpolation process unit 205b which then applies an interpolation process of data to the missing ultrasonic echo signal due to a defect element among the input ultrasonic echo signals and outputs the interpolation-processed ultrasonic echo signal 206.

FIG. 19 is a diagram describing a function of a data interpolation process unit according to the present embodiment. As described above, ultrasonic echo signals S1 through $S_{i-2}$, $S_{i-1}$, $S_i$, $S_{i+1}$, $S_{i+2}$ through $S_n$ are output from the respective cMUT elements 201. Here, the present embodiment assumes that the i-th cMUT 201 element has defect. Consequently, there is no output from the i-th cMUT 201 element.

The data interpolation process unit 205b receives the ultrasonic echo signals from the respective cMUT elements 201 and outputs the received signals as is. In the description in FIG. 19, the received ultrasonic echo signals S1 through $S_{i-2}$, $S_{i-1}$, $S_i$, $S_{i+1}$, $S_{i+2}$ through $S_n$ are output as is.

An ultrasonic echo signal $S_i$ to be output from the i-th cMUT elements 201, however, is not input into the data interpolation process unit 205b, and therefore it is missing because the i-th cMUT elements 201 is a defect element. The data interpolation process unit 205b accordingly generates a pseudo signal corresponding to the missing ultrasonic echo signal $S_i$ by performing an interpolation process.

Figure 20:
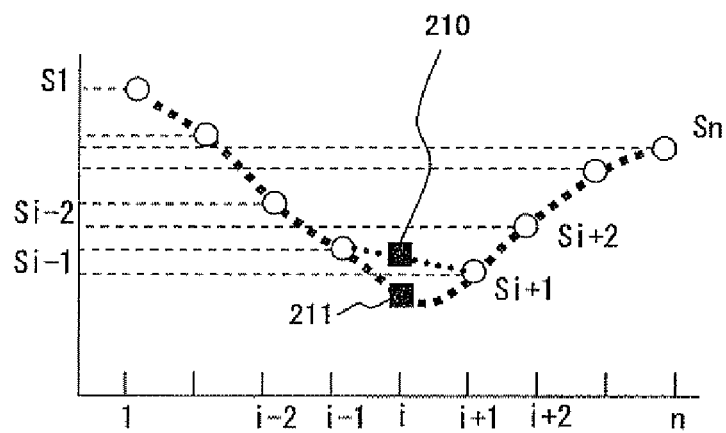
FIG. 20 is an explanation drawing for an interpolation calculation at a data interpolation unit 205 according to the fourth embodiment.

FIG. 20 is a diagram describing an interpolation process calculation at a data interpolation process unit 205 according to the present embodiment. The horizontal axis shows the first through nth cMUT elements 201. The vertical axis shows the voltages of the ultrasonic echo signals input into the data interpolation process unit 205, indicating the voltages of the ultrasonic echo signals corresponding to the respective cMUT elements 201.

Except for the i-th cMUT 201 element, the ultrasonic echo signals corresponding to the first through nth cMUT elements 201 are input into the data interpolation process unit 205b. The data interpolation process unit 205b accordingly generates a pseudo signal corresponding to the ultrasonic echo signal to be output from the i-th cMUT element 201 via interpolation.

One example of a method for an interpolation is using an average. In the case of FIG. 20, the average of the signals $S_{i-1}$ and $S_{i+1}$ on either side of the missing ultrasonic echo signal $S_i$ is calculated, thereby obtaining a pseudo signal 210.

Alternatively, another interpolation method, e.g., the Lagrange interpolation, the Newton interpolation and the method of least squares, may be used for improving the accuracy of a pseudo signal. This makes it possible to obtain a pseudo signal 211.

As described above, the present invention is contrived to comprise means for detecting a position of an abnormal vibrating element, means for generating a pseudo transducer element at the aforementioned position, and means for building up an ultrasound diagnosis image by using the calculated information from the pseudo transducer element.

The simulation information is information obtained by averaging the information from normal transducer elements adjacent to the surrounding position of the defect transducer element. Alternatively, the calculated data may be an information obtained by interpolating the data from a normal transducer element most adjacent to the surrounding position of the abnormal transducer element and the information from a normal transducer element next to the aforementioned normal transducer element.

Alternatively, an extrapolation process may be applied, in place of an interpolation process, as means for generating a pseudo signal.

This alternative method draws an ultrasound diagnosis image temporarily, detecting a zone with abnormal brightness by means of an image process and correcting the brightness by means of an image process, in place of generating a simulated signal by focusing on the reception signal as described above.

As such, even if an ultrasonic echo signal of a spot corresponding to a defect element or subelement is not obtainable, an ultrasound diagnosis image can be generated by complementing the ultrasonic echo signal, thereby making it possible to minimize degradation in image quality of the ultrasound diagnosis image.

The use of the present invention makes it possible to detect a defect cell, defect element or subelement and connect only the electrodes of normal cells, subelement or elements, other than the defect cell, defect element or subelement, thereby avoiding inoperability as a result of the entirety of elements or the entirety of ultrasonic transducer shorting.

What is claimed is:

1. A capacitive micromachined ultrasonic transducer (cMUT) which is constituted by a plurality of transducer elements comprising plural transducer cells or plural subelements that are mutually connected in parallel and which comprises:
    a silicon substrate;
    a bottom electrode placed on the silicon substrate;
    an upper electrode placed opposite to the bottom electrode and separated therefrom by a prescribed air or vacuum gap;
    a membrane for supporting the upper electrode; and
    a membrane supporting part for supporting the membrane, wherein
    the cMUT comprises
    a first electrode pad corresponding to either one of the transducer cells, each of a plurality of transducer subelement constituted by a group of the transducer cells or each of the transducer elements and which has an electrical continuity to the upper electrode,
    a second electrode pad which is a ground electrode electrically connected to the upper electrode, and
    a signal wire for receiving an input of a drive signal for driving the transducer element, wherein
    the signal wire has an electrical continuity only to the first electrode pad that is not in a state of short-circuit to the second electrode pad.

2. The cMUT according to claim 1, wherein the first electrode pad is featured on the same surface side as the second electrode pad.

3. The cMUT according to claim 2, wherein the side on which the first electrode pad and second electrode pad are featured is a side for transmitting and receiving an ultrasound.

4. A body tissue insertion type ultrasonic diagnosis apparatus comprising a cMUT according to claim 1.

5. A production method for a capacitive micromachined ultrasonic transducer (cMUT) which is constituted by a plurality of transducer elements comprising plural transducer cells or plural transducer subelements that are mutually connected in parallel and which comprises a silicon substrate, a bottom electrode placed on the silicon substrate, an upper electrode placed opposite to the bottom electrode and separated therefrom by a prescribed air or vacuum gap, a membrane for supporting the upper electrode and a membrane supporting part for supporting the membrane, wherein the production method including:
    a first electrode pad corresponding to either of the transducer cells, each of a plurality of transducer subelement constituted by a group of the transducer cells or each of the transducer elements and which has an electrical continuity to the bottom electrode;
    a second electrode pad which is a ground electrode electrically connected to the upper electrode, and
    electrically connecting an input wire receiving an input of a drive signal for driving the transducer element only to the first electrode pad which is not in short-circuit to the second electrode pad on the basis of the detection result of detecting whether or not there is a shorting between the first and second electrode pads.

6. The production method for a cMUT according to claim 5, featuring the first and second electrode pads on the same surface side.

7. The production method for a cMUT according to claim 6, featuring the first and second electrode pads on a surface transmitting and receiving an ultrasound.

8. The production method for a cMUT according to claim 5, wherein the detection of shorting detects the capacitance and dielectric loss between the first and second electrode pads by applying a voltage between them.

9. The production method for a cMUT according to claim 5, wherein the detection of shorting detects the capacitance and dielectric loss between the first and second electrode pads by applying an alternate current (AC) voltage and a direct current (DC) voltage between them.

10. The production method for a cMUT according to claim 5, wherein the detection of shorting detects the DC resistance between the first and second electrode pads by applying a voltage between them.

11. The production method for a cMUT according to claim 5, inspecting a noncontact infrared radiation by applying a voltage between the first and second electrode pads in the detection of shorting.

12. The production method for a cMUT according to claim 5, wherein the detection of shorting is an imaging method using an electron beam.

13. The production method for a cMUT according to claim 12, wherein the imaging method is at least either a potential contrast method, a specimen-absorbed current method, a resistance contrast (RC) method, or an electron beam-induced current method.

14. A body tissue insertion type ultrasonic diagnosis apparatus comprising a cMUT produced by the production method therefor according to claim 5.

15. A production method for a capacitive micromachined ultrasonic transducer (cMUT) which is constituted by a plurality of transducer elements comprising plural transducer cells or plural transducer subelements that are mutually connected in parallel and which comprises a silicon substrate, a bottom electrode placed on the silicon substrate, an upper electrode placed opposite to the bottom electrode and separated therefrom by a prescribed air or vacuum gap, a membrane for supporting the upper electrode and a membrane supporting part for supporting the membrane, wherein the production method including:
    a first electrode pad corresponding to either of the transducer cells, each of a plurality of transducer subelement constituted by a group of the transducer cells or each of the transducer elements and which has an electrical continuity to the bottom electrode;
    a second electrode pad which is a ground electrode electrically connected to the upper electrode, and
    electrically cutting the signal wire off the first electrode pad which is in short-circuit to the second electrode pad on the basis of a result of detecting whether or not there is a shorting between the first and second electrode pads after electrically connecting a signal wire, which is for receiving an input of a drive signal for driving the transducer element, to all of the first electrode pads.

16. The production method for a cMUT according to claim 15, wherein a noncontact infrared of a temperature distribution is inspected during the detection of shorting by applying a voltage between the first and second electrode pads.

17. The production method for a cMUT according to claim 15, wherein the detection of shorting is done by an imaging method using an electron beam.

18. The production method for a cMUT according to claim 17, wherein the imaging method is at least either a potential contrast method, a specimen-absorbed current method, a resistance contrast (RC) method, or an electron-beam induced current method.

19. A body tissue insertion type ultrasonic diagnosis apparatus comprising a cMUT produced by the production method therefor according to claim 15.

20. The production method for a cMUT according to claim 15, featuring the first and second electrode pads on the same surface side.

21. The production method for a cMUT according to claim 20, featuring the first and second electrode pads on a surface transmitting and receiving an ultrasound.

22. A body tissue insertion type ultrasonic diagnosis apparatus having an ultrasonic transducer element incorporating a capacitive micromachined ultrasonic transducer (cMUT) arraying a plurality of ultrasonic transducer elements, comprising:
 a position detector for detecting position information of the ultrasonic transducer element on the basis of an ultrasonic echo signal obtained from each of the ultrasonic transducer elements;
 a analog/digital (A/D) converter for simulatively generating an ultrasonic echo signal for complementing a missing ultrasonic echo signal if there is a missing one; and
 an imaging unit for building up an ultrasonic diagnosis image on the basis of a simulated ultrasonic echo signal generated by the analog/digital (A/D) converter.

23. The body tissue insertion type ultrasonic diagnosis apparatus according to claim 22, wherein
 the cMUT comprises a silicon substrate; a bottom electrode placed on the silicon substrate; an upper electrode placed opposite to the bottom electrode and separate therefrom by a prescribed air or vacuum gap; a membrane for supporting the upper electrode;
 and a membrane supporting part for supporting the membrane, wherein a plurality of transducer elements, in which terminals of individual transducer cells are mutually connected to one another in parallel, are integratedly arrayed and the cMUT is comprised at the tip of the transducer elements.

24. The body tissue insertion type ultrasonic diagnosis apparatus according to claim 23, wherein
 the cMUT comprises
 a first electrode pad corresponding to each of the transducer elements and which has an electrical continuity to the bottom electrode,
 a second electrode pad which is a ground electrode electrically connected to the upper electrode, wherein
 the signal wire has an electrical continuity only to the first electrode pad in which the terminal of the second electrode pad is not in short-circuit to that of the transducer element.

25. The body tissue insertion type ultrasonic diagnosis apparatus according to claim 22, wherein
 the analog/digital (A/D) converter generates the simulated signal by calculating an average of peak voltages of the ultrasonic echo signal obtained from a transducer element adjacent to the transducer element which has missed the ultrasonic echo signal.

26. The body tissue insertion type ultrasonic diagnosis apparatus according to claim 22, wherein
 the analog/digital (A/D) converter applies an insertion interpolation process to the detected ultrasonic echo signal, if there is a missing signal, and generates a pseudo signal corresponding to the missing signal.

27. A capacitive micromachined ultrasonic transducer (cMUT) which is constituted by a plurality of transducer elements or subelements comprising plural transducer cells that are mutually connected in parallel and which comprises:
 a silicon substrate;
 a bottom electrode placed on the silicon substrate;
 an upper electrode placed opposite to the bottom electrode and separated therefrom by a prescribed air or vacuum gap;
 a membrane for supporting the upper electrode; and
 a membrane supporting part for supporting the membrane, wherein
 the cMUT is configured by a two-terminal construction which is constituted of
 a first electrode pad which is the one corresponding to each of the transducer subelement, a plurality of which comprise an aggregation of the existing transducer cells and have an electrical continuity to the bottom electrode,
 a second electrode pad which is a ground electrode electrically connected to the upper electrode,
 a first terminal electrically connected to all of the first electrode pads,
 a second terminal electrically connected to all of the second electrode pads, and
 a signal wire for receiving an input of a drive signal for driving the transducer element, wherein
 the signal wire has an electrical continuity only to the first electrode pad that is not in a state of short-circuit to the second electrode pad.

* * * * *